US009107958B2

(12) United States Patent
Wightman

(10) Patent No.: US 9,107,958 B2

(45) Date of Patent: Aug. 18, 2015

(54) HYDRAZINO 1H-IMIDAZOQUINOLIN-4-AMINES AND CONJUGATES MADE THEREFROM

(75) Inventor: Paul D. Wightman, Louisville, KY (US)

(73) Assignee: 3M Innovative Properties Company, St. Paul, MN (US)

(*) Notice: Subject to any disclaimer, the term of this patent is extended or adjusted under 35 U.S.C. 154(b) by 66 days.

(21) Appl. No.: 14/123,718

(22) PCT Filed: Jun. 1, 2012

(86) PCT No.: PCT/US2012/040461

§ 371 (c)(1), (2), (4) Date: Apr. 23, 2014

(87) PCT Pub. No.: WO2012/167081

PCT Pub. Date: Dec. 6, 2012

(65) Prior Publication Data

US 2014/0286988 A1 Sep. 25, 2014

Related U.S. Application Data

(60) Provisional application No. 61/493,051, filed on Jun. 3, 2011, provisional application No. 61/493,143, filed on Jun. 3, 2011.

(51) Int. Cl.

| | |
|---|---|
| ***A61K 38/00*** | (2006.01) |
| ***A61K 47/48*** | (2006.01) |
| ***C07D 471/04*** | (2006.01) |
| ***A61K 39/145*** | (2006.01) |

(52) U.S. Cl.

CPC ......... *A61K 47/48261* (2013.01); *A61K 39/145* (2013.01); *A61K 47/48061* (2013.01); *C07D 471/04* (2013.01)

(58) Field of Classification Search

CPC ............................... A61K 38/00; A61K 39/00

See application file for complete search history.

(56) References Cited

U.S. PATENT DOCUMENTS

| | | | |
|---|---|---|---|
| 3,314,941 | A | 4/1967 | Littell et al. |
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,206,370 | A | 4/1993 | Schwartz |
| 5,238,944 | A | 8/1993 | Wick et al. |
| 5,266,575 | A | 11/1993 | Gerster |
| 5,268,376 | A | 12/1993 | Gester |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,444,065 | A | 8/1995 | Nikolaides et al. |
| 5,446,153 | A | 8/1995 | Lindstrom et al. |
| 5,482,936 | A | 1/1996 | Lindstrom |
| 5,494,916 | A | 2/1996 | Lindstrom et al. |
| 5,525,612 | A | 6/1996 | Gerster |
| 5,605,899 | A | 2/1997 | Gerster |
| 5,627,281 | A | 5/1997 | Nikolaides et al. |
| 5,644,063 | A | 7/1997 | Lindstrom et al. |
| 5,648,516 | A | 7/1997 | Nikolaides et al. |
| 5,679,778 | A | 10/1997 | Abrams |
| 5,693,811 | A | 12/1997 | Lindstrom |
| 5,714,608 | A | 2/1998 | Gerster |
| 5,741,908 | A | 4/1998 | Gerster et al. |
| 5,756,747 | A | 5/1998 | Gerster et al. |
| 5,886,006 | A | 3/1999 | Nikolaides et al. |
| 5,939,090 | A | 8/1999 | Beaurline et al. |
| 6,028,076 | A | 2/2000 | Hirota |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,113,918 | A | 9/2000 | Johnson |
| 6,194,388 | B1 | 2/2001 | Krieg |

(Continued)

FOREIGN PATENT DOCUMENTS

| | | |
|---|---|---|
| EP | 0 394 026 | 10/1990 |
| EP | 1 104 764 | 6/2001 |

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, June/July, 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem*. 15, pp. 1278-1284 (1950).

(Continued)

*Primary Examiner* — Marcela M Cordero Garcia

*Assistant Examiner* — Kaipeen Yang

(57) ABSTRACT

1H-Imidazo[4,5-c]quinolin-4-amines substituted at the 1-position with a substituent bearing a hydrazinobenzamide or hydrazinonicotinamide, a salt thereof, or a protected hydrazinobenzamide or hydrazinonicotinamide and conjugates made from such compounds are disclosed. Pharmaceutical compositions containing the compound or the conjugate, methods of making a conjugate, and methods of use of the compounds or conjugates as immunomodulators for inducing cytokine biosynthesis in an animal and for vaccinating an animal are also disclosed.

20 Claims, No Drawings

(56) References Cited

U.S. PATENT DOCUMENTS 6,194,425 B1 2/2001 Gerster et al.
6,200,592 B1 3/2001 Tomai et al.
6,207,646 B1 3/2001 Krieg
6,239,116 B1 5/2001 Krieg
6,245,776 B1 6/2001 Skwierczynski et al.
6,303,347 B1 10/2001 Johnson
6,329,381 B1 12/2001 Kurimoto
6,331,539 B1 12/2001 Crooks et al.
6,339,068 B1 1/2002 Krieg
6,365,166 B2 4/2002 Beaurline et al.
6,376,501 B1 4/2002 Isobe
6,376,669 B1 4/2002 Rice et al.
6,387,938 B1 5/2002 Mizuguchi
6,406,705 B1 6/2002 Davis
6,426,334 B1 7/2002 Agrawal
6,440,992 B1 8/2002 Gerster et al.
6,451,810 B1 9/2002 Coleman et al.
6,476,000 B1 11/2002 Agrawal
6,486,168 B1 11/2002 Skwierczynski et al.
6,514,985 B1 2/2003 Gerster et al.
6,518,265 B1 2/2003 Kato et al.
6,525,028 B1 2/2003 Johnson
6,525,064 B1 2/2003 Dellaria et al.
6,541,485 B1 4/2003 Crooks et al.
6,545,016 B1 4/2003 Dellaria et al.
6,545,017 B1 4/2003 Dellaria et al.
6,558,951 B1 5/2003 Tomai et al.
6,573,273 B1 6/2003 Crooks et al.
6,610,319 B2 8/2003 Tomai et al.
6,627,638 B2 9/2003 Gerster et al.
6,627,640 B2 9/2003 Gerster et al.
6,630,588 B2 10/2003 Rice et al.
6,638,944 B2 10/2003 Mickelson
6,649,172 B2 11/2003 Johnson
6,656,938 B2 12/2003 Crooks et al.
6,660,735 B2 12/2003 Crooks et al.
6,660,747 B2 12/2003 Crooks et al.
6,664,260 B2 12/2003 Charles et al.
6,664,264 B2 12/2003 Dellaria et al.
6,664,265 B2 12/2003 Crooks et al.
6,667,312 B2 12/2003 Bonk et al.
6,670,372 B2 12/2003 Charles et al.
6,677,347 B2 1/2004 Crooks et al.
6,677,348 B2 1/2004 Heppner et al.
6,677,349 B1 1/2004 Griesgraber
6,683,088 B2 1/2004 Crooks et al.
6,696,076 B2 2/2004 Tomai et al.
6,696,465 B2 2/2004 Dellaria et al.
6,703,402 B2 3/2004 Gerster et al.
6,706,728 B2 3/2004 Hedenstrom et al.
6,716,988 B2 4/2004 Dellaria et al.
6,720,333 B2 4/2004 Dellaria et al.
6,720,334 B2 4/2004 Dellaria et al.
6,720,422 B2 4/2004 Dellaria et al.
6,743,920 B2 6/2004 Lindstrom et al.
6,756,382 B2 6/2004 Coleman et al.
6,784,188 B2 8/2004 Crooks et al.
6,797,718 B2 9/2004 Dellaria et al.
6,800,624 B2 10/2004 Crooks et al.
6,800,728 B2 10/2004 Schwartz
6,809,203 B2 10/2004 Gerster et al.
6,818,650 B2 11/2004 Griesgraber
6,825,350 B2 11/2004 Crooks et al.
6,841,678 B2 1/2005 Merli et al.
6,852,861 B2 2/2005 Merli et al.
6,878,719 B2 4/2005 Lindstrom et al.
6,888,000 B2 5/2005 Crooks et al.
6,894,060 B2 5/2005 Slade
6,897,221 B2 5/2005 Crooks et al.
6,903,113 B2 6/2005 Heppner et al.
6,916,925 B1 7/2005 Rice et al.
6,921,826 B2 7/2005 Dellaria et al.
6,924,293 B2 8/2005 Lindstrom
6,943,225 B2 9/2005 Lee et al.
6,949,649 B2 9/2005 Bonk et al.
6,953,804 B2 10/2005 Dellaria et al.
6,969,722 B2 11/2005 Heppner et al.
6,989,389 B2 1/2006 Heppner et al.
7,030,129 B2 4/2006 Miller et al.
7,030,131 B2 4/2006 Crooks et al.
7,038,053 B2 5/2006 Lindstrom et al.
7,049,439 B2 5/2006 Crooks et al.
7,078,523 B2 7/2006 Crooks et al.
7,091,214 B2 8/2006 Hays et al.
7,098,221 B2 8/2006 Heppner et al.
7,112,677 B2 9/2006 Griesgraber
7,115,622 B2 10/2006 Crooks et al.
7,125,890 B2 10/2006 Dellaria et al.
7,132,429 B2 11/2006 Griesgraber et al.
7,132,438 B2 11/2006 Frenkel et al.
7,148,232 B2 12/2006 Gerster et al.
7,157,453 B2 1/2007 Crooks et al.
7,163,947 B2 1/2007 Griesgraber et al.
7,179,253 B2 2/2007 Graham et al.
7,199,131 B2 4/2007 Lindstrom
7,214,675 B2 5/2007 Griesgraber
7,220,758 B2 5/2007 Dellaria et al.
7,226,928 B2 6/2007 Mitra et al.
7,276,515 B2 10/2007 Dellaria et al.
7,288,550 B2 10/2007 Dellaria et al.
7,301,027 B2 11/2007 Colombo et al.
7,375,180 B2 5/2008 Gorden et al.
7,387,271 B2 6/2008 Noelle et al.
7,393,859 B2 7/2008 Coleman et al.
7,427,629 B2 9/2008 Kedl et al.
7,462,689 B2 12/2008 Schwartz
7,485,432 B2 2/2009 Fink et al.
7,544,697 B2 6/2009 Hays et al.
7,576,068 B2 8/2009 Averett
7,578,170 B2 8/2009 Mayer et al.
7,579,359 B2 8/2009 Krepski et al.
7,598,382 B2 10/2009 Hays et al.
7,612,083 B2 11/2009 Griesgraber
7,648,997 B2 1/2010 Kshirsagar et al.
7,655,672 B2 2/2010 Statham et al.
7,687,628 B2 3/2010 Gutman et al.
7,696,159 B2 4/2010 Owens et al.
7,699,057 B2 4/2010 Miller et al.
7,731,967 B2 6/2010 O'Hagan et al.
7,799,800 B2 9/2010 Wightman
7,879,849 B2 2/2011 Hays et al.
7,884,207 B2 2/2011 Stoermer et al.
7,888,349 B2 2/2011 Kshirsagar et al.
7,897,597 B2 3/2011 Lindstrom et al.
7,897,609 B2 3/2011 Niwas et al.
7,897,767 B2 3/2011 Kshirsagar et al.
7,902,209 B2 3/2011 Statham et al.
7,902,210 B2 3/2011 Statham et al.
7,902,211 B2 3/2011 Statham et al.
7,902,212 B2 3/2011 Statham et al.
7,902,213 B2 3/2011 Statham et al.
7,902,214 B2 3/2011 Statham et al.
7,902,215 B2 3/2011 Statham et al.
7,902,216 B2 3/2011 Statham et al.
7,902,242 B2 3/2011 Statham et al.
7,902,243 B2 3/2011 Statham et al.
7,902,244 B2 3/2011 Statham et al.
7,902,245 B2 3/2011 Statham et al.
7,902,246 B2 3/2011 Statham et al.
7,906,506 B2 3/2011 Griesgraber et al.
7,915,281 B2 3/2011 Moser et al.
7,939,526 B2 5/2011 Radmer et al.
7,943,609 B2 5/2011 Griesgraber et al.
7,943,610 B2 5/2011 Hays et al.
7,943,636 B2 5/2011 Hays et al.
7,968,562 B2 6/2011 Skwierczynski et al.
7,968,563 B2 6/2011 Kshirsagar et al.
7,993,659 B2 8/2011 Noelle et al.
8,017,779 B2 9/2011 Merrill et al.
8,026,366 B2 9/2011 Prince et al.
8,034,938 B2 10/2011 Griesgraber et al.
8,138,173 B2 3/2012 Merrill et al.
8,143,270 B2 3/2012 Kshirsagar et al.
8,158,794 B2 4/2012 Kshirsagar et al.

(56) References Cited

U.S. PATENT DOCUMENTS

| | | | |
|---|---|---|---|
| 8,178,677 | B2 | 5/2012 | Kshirsagar et al. |
| 8,658,666 | B2 | 2/2014 | Rice et al. |
| 8,673,932 | B2 | 3/2014 | Kshirsagar et al. |
| 8,691,837 | B2 | 4/2014 | Krepski et al. |
| 8,697,873 | B2 | 4/2014 | Krepski et al. |
| 8,735,421 | B2 | 5/2014 | Bonk et al. |
| 8,802,853 | B2 | 8/2014 | Bonk et al. |
| 8,871,782 | B2 | 10/2014 | Lindstrom et al. |
| 2002/0055517 | A1 | 5/2002 | Smith |
| 2002/0058674 | A1 | 5/2002 | Hedenstrom et al. |
| 2002/0107262 | A1 | 8/2002 | Lindstrom |
| 2003/0133913 | A1 | 7/2003 | Tomai et al. |
| 2003/0139364 | A1 | 7/2003 | Krieg et al. |
| 2003/0199461 | A1 | 10/2003 | Averett |
| 2004/0014779 | A1 | 1/2004 | Gorden et al. |
| 2004/0132079 | A1 | 7/2004 | Gupta et al. |
| 2004/0175336 | A1 | 9/2004 | Egging et al. |
| 2004/0180919 | A1 | 9/2004 | Lee et al. |
| 2004/0191833 | A1 | 9/2004 | Fink et al. |
| 2004/0197865 | A1 | 10/2004 | Gupta et al. |
| 2004/0202720 | A1 | 10/2004 | Wightman et al. |
| 2004/0214851 | A1 | 10/2004 | Birmachu et al. |
| 2004/0258698 | A1 | 12/2004 | Wightman et al. |
| 2004/0265351 | A1 | 12/2004 | Miller et al. |
| 2005/0048072 | A1 | 3/2005 | Kedl et al. |
| 2005/0059072 | A1 | 3/2005 | Birmachu et al. |
| 2005/0070460 | A1 | 3/2005 | Hammerbeck et al. |
| 2005/0096259 | A1 | 5/2005 | Tomai et al. |
| 2005/0106300 | A1 | 5/2005 | Chen et al. |
| 2005/0136065 | A1 | 6/2005 | Valiante |
| 2005/0158325 | A1 | 7/2005 | Hammerbeck et al. |
| 2005/0165043 | A1 | 7/2005 | Miller et al. |
| 2005/0171072 | A1 | 8/2005 | Tomai et al. |
| 2005/0175630 | A1 | 8/2005 | Raz et al. |
| 2005/0239735 | A1 | 10/2005 | Miller et al. |
| 2005/0245562 | A1 | 11/2005 | Garcia-Echeverria et al. |
| 2006/0045885 | A1 | 3/2006 | Kedl et al. |
| 2006/0045886 | A1 | 3/2006 | Kedl |
| 2006/0051374 | A1 | 3/2006 | Miller et al. |
| 2006/0088542 | A1 | 4/2006 | Braun |
| 2006/0142202 | A1 | 6/2006 | Alkan et al. |
| 2006/0142235 | A1 | 6/2006 | Miller et al. |
| 2006/0195067 | A1 | 8/2006 | Wolter et al. |
| 2006/0216333 | A1 | 9/2006 | Miller et al. |
| 2007/0078121 | A1 | 4/2007 | Flynn et al. |
| 2007/0099901 | A1 | 5/2007 | Krepski et al. |
| 2007/0123559 | A1 | 5/2007 | Statham et al. |
| 2007/0166384 | A1 | 7/2007 | Zarraga et al. |
| 2007/0167479 | A1 | 7/2007 | Busch et al. |
| 2007/0213355 | A1 | 9/2007 | Capraro et al. |
| 2007/0243215 | A1 | 10/2007 | Miller et al. |
| 2007/0259881 | A1 | 11/2007 | Dellaria et al. |
| 2007/0259907 | A1 | 11/2007 | Prince |
| 2007/0292456 | A1 | 12/2007 | Hammerbeck et al. |
| 2008/0015184 | A1 | 1/2008 | Kshirsagar et al. |
| 2008/0039533 | A1 | 2/2008 | Sahouani et al. |
| 2008/0063714 | A1 | 3/2008 | Sahouani et al. |
| 2008/0119508 | A1 | 5/2008 | Slade et al. |
| 2008/0188513 | A1 | 8/2008 | Skwierczynski et al. |
| 2008/0193468 | A1 | 8/2008 | Levy et al. |
| 2008/0193474 | A1 | 8/2008 | Griesgraber et al. |
| 2008/0207674 | A1 | 8/2008 | Stoesz et al. |
| 2008/0213308 | A1 | 9/2008 | Valiante et al. |
| 2008/0262021 | A1 | 10/2008 | Capraro et al. |
| 2008/0262022 | A1 | 10/2008 | Lee et al. |
| 2008/0306252 | A1 | 12/2008 | Crooks et al. |
| 2008/0306266 | A1 | 12/2008 | Martin et al. |
| 2008/0312434 | A1 | 12/2008 | Lindstrom et al. |
| 2008/0318998 | A1 | 12/2008 | Prince et al. |
| 2009/0005371 | A1 | 1/2009 | Rice et al. |
| 2009/0017076 | A1 | 1/2009 | Miller et al. |
| 2009/0023722 | A1 | 1/2009 | Coleman et al. |
| 2009/0030031 | A1 | 1/2009 | Kshirsagar et al. |
| 2009/0035323 | A1 | 2/2009 | Stoermer et al. |
| 2009/0075980 | A1 | 3/2009 | Hays et al. |
| 2009/0105295 | A1 | 4/2009 | Kshirsagar et al. |
| 2009/0124652 | A1 | 5/2009 | Ach et al. |
| 2009/0163532 | A1 | 6/2009 | Perman et al. |
| 2009/0176821 | A1 | 7/2009 | Kshirsagar et al. |
| 2009/0202443 | A1 | 8/2009 | Miller et al. |
| 2009/0221551 | A1 | 9/2009 | Kshirsagar et al. |
| 2009/0221556 | A1 | 9/2009 | Kshirsagar et al. |
| 2009/0240055 | A1 | 9/2009 | Krepski et al. |
| 2009/0246174 | A1 | 10/2009 | Rook et al. |
| 2009/0253695 | A1 | 10/2009 | Kshirsagar et al. |
| 2009/0270443 | A1 | 10/2009 | Stoermer et al. |
| 2009/0298821 | A1 | 12/2009 | Kshirsagar et al. |
| 2009/0306388 | A1 | 12/2009 | Zimmerman et al. |
| 2010/0028381 | A1 | 2/2010 | Gorski et al. |
| 2010/0056557 | A1 | 3/2010 | Benninghoff et al. |
| 2010/0096287 | A1 | 4/2010 | Stoesz et al. |
| 2010/0113565 | A1 | 5/2010 | Gorden et al. |
| 2010/0152230 | A1 | 6/2010 | Dellaria et al. |
| 2010/0158928 | A1 | 6/2010 | Stoermer et al. |
| 2010/0173906 | A1 | 7/2010 | Griesgraber |
| 2010/0180902 | A1 | 7/2010 | Miller et al. |
| 2010/0240693 | A1 | 9/2010 | Lundquist et al. |
| 2011/0021554 | A1 | 1/2011 | Stoesz et al. |
| 2014/0227317 | A1 | 8/2014 | Wightman |

FOREIGN PATENT DOCUMENTS

| | | |
|---|---|---|
| JP | 9-176116 | 7/1997 |
| JP | 9-208584 | 8/1997 |
| JP | 11-080156 | 3/1999 |
| JP | 11-222432 | 8/1999 |
| JP | 2000-247884 | 9/2000 |
| WO | WO 00-75304 | 12/2000 |
| WO | WO 02-08905 | 1/2002 |
| WO | WO 02-24225 | 3/2002 |
| WO | WO 02-36592 | 5/2002 |
| WO | WO 2005-003064 | 1/2005 |
| WO | WO 2006-028451 | 3/2006 |
| WO | WO 2006-063072 | 6/2006 |
| WO | WO 2006-121528 | 11/2006 |
| WO | WO 2007-030775 | 3/2007 |

OTHER PUBLICATIONS

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

Gundlach, "Synthesis and Evaluation of an Anti-MLCI × Anti-CD90 Bispecific Antibody for Targeting and Retaining Bone-Marrow-Derived Multipotent Stromal Cells in Infarcted Myocardium", Bioconjugate Chemistry, Jul. 2011, vol. 22, pp. 1706-1714.

Heil, "Species-Specific Recognition of Single-Stranded RNA via Toll-like Receptor 7 and 8", Science, Mar. 2004, vol. 303, No. 5663, pp. 1526-1529.

International Search Report for PCT International Application No. PCT/US2012/040461, mailed on Jul. 25, 2012, 14 pages.

Iyer, "Aromatic Aldehyde and Hydrazine Activated Peptide Coated Quantum Dots for Easy Bioconjugation and Live Cell Imaging", Bioconjugate Chemistry, May 2011, vol. 22, pp. 1006-1011.

Lagisetty, "Synthesis of radiolabeled cytarabine conjugates", Biorganic and Medicinal Chemistry Letters, Aug. 2009, vol. 19, No. 16, pp. 4764-4767.

(56) References Cited

OTHER PUBLICATIONS

Park, "Sodium Dithionite Reduction of Nitroarenes Using Viologen as an Electron Phase-Transfer Catalyst" Tetrahedron Letters, 1993, vol. 34, No. 46, pp. 7445-7446.

Pegurier, "Pyrazolone methylamino piperidine derivatives as novel CCR3 antagonists", Bioorganic and Medicinal Chemistry Letters, 2007, vol. 17, No. 15, pp. 4228-4231.

Riener, "Heterobifunctional crosslinkers for tethering single ligand molecules to scanning probes", Analytica. Chimica Acta, 2003, vol. 497, No. 1-2, pp. 101-114.

Surrey, "The Synthesis of Some 3-Nitro- and 3-Amino-4-dialkylaminoalkylaminoquinoline Derivatives". Journal of the American Chemical Society, Jun. 1951, vol. 73, No. 6, pp. 2413-2416.

Supplemental European Search Report from Application No. EP12793123, dated Sep. 9, 2014, 3 pages.

Gerster et al. "Synthesis and Structure" *J. Med Chem.* 2005, 48, 3481-3491.

HYDRAZINO 1H-IMIDAZOQUINOLIN-4-AMINES AND CONJUGATES MADE THEREFROM

CROSS REFERENCE TO RELATED APPLICATIONS

This application is a national stage filing under U.S.C. 371 of PCT/US2012/040461, filed Jun. 1, 2012, which claims priority to U.S. Provisional Application Nos. 61/493,051 and 61/493,143 both filed Jun. 3, 2011, the disclosures of which are incorporated by reference in their entirety herein.

BACKGROUND

There has been an effort in recent years, with significant success, to discover new drug compounds that act by stimulating certain key aspects of the immune system, as well as by suppressing certain other aspects (see, e.g., U.S. Pat. No. 6,039,969 (Tomai et al.) and U.S. Pat. No. 6,200,592 (Tomai et al.). These compounds, referred to herein as immune response modifiers (IRMs), appear to act through basic immune system mechanisms known as Toll-like receptors (TLRs) to induce selected cytokine biosynthesis, induction of co-stimulatory molecules, and increased antigen-presenting capacity.

Many IRMs may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), $T_H2$-mediated diseases (e.g., asthma, allergic rhinitis, atopic dermatitis), and auto-immune diseases.

Certain IRMs may also be useful, for example, as vaccine adjuvants. In some cases, an IRM compound may be administered in a conjugated composition in which the IRM compound is covalently attached to an antigenic moiety (see, e.g., U.S. Pat. No. 7,427,629 (Kedl et al.) and U.S. Pat. Appl. Pub. No. 2009/0035323 (Stoermer et al.)).

Many known IRMs are imidazoquinoline amine derivatives (see, e.g., U.S. Pat. No. 4,689,338 (Gerster)), but other compound classes are known as well (see, e.g., U.S. Pat. No. 5,446,153 (Lindstrom et al.); U.S. Pat. No. 6,194,425 (Gerster et al.); and U.S. Pat. No. 6,110,929 (Gerster et al.); and International Publication Number WO2005/079195 (Hays et al.)) while more are still being discovered.

In view of the great therapeutic potential for IRMs in the treatment of a wide variety of diseases and conditions, and despite the important work that has already been done, there is still a need for new compounds that can modulate the immune response and for expanded uses, compositions, and delivery options for IRM compounds.

SUMMARY

The present invention provides new compounds useful, for example, for making IRM conjugates and inducing cytokine biosynthesis in animals. Such compounds have the following formula (I):

I

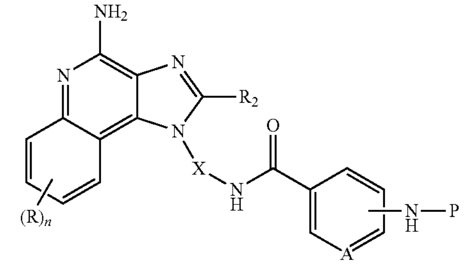

wherein R, $R_2$, A, X, P, and n are as defined below.

In another aspect, the present invention provides a conjugate comprising a reaction product of the compound or salt of formula I and an aldehyde-bearing antigen.

In another aspect, the present invention provides a conjugate of an antigen, the conjugate having at least one segment represented by formula (II):

II

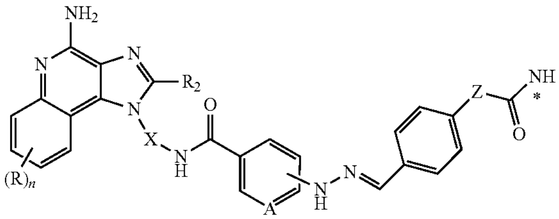

wherein R, $R_2$, A, X, n, Z and the antigen are as defined below.

The compounds of Formula I are useful as immune response modifiers due to their ability to induce cytokine biosynthesis (e.g., induce the synthesis of at least one cytokine) and otherwise modulate the immune response when administered to animals. Compounds of Formula I are also useful vaccine adjuvants that can be covalently joined with antigens to provide conjugates (e.g., conjugates having at least one segment represented by Formula II). Co-delivering a vaccine adjuvant (e.g., an IRM compound such as a compound of Formula I) and an antigen to an immune cell can increase the immune response to the antigen and improve antigen-specific immunological memory. Optimal delivery may occur, for example, when the adjuvant and the antigen are processed within an antigen presenting cell at the same time.

Advantageously, conjugates according to the present invention can be prepared under conditions that do not denature the antigens (e.g., which may be proteins). For example, the conjugates can be prepared at physiological pH. Furthermore, the covalent bonds formed to link the compounds of Formula I and the antigen in the synthesis of the conjugates do not require irradiation. Also advantageously, in many embodiments, the reaction of the compound of Formula I and an aldehyde-bearing antigen can be easily monitored using UV spectroscopy due to the characteristic absorption of the hydrazone bond that is formed.

The ability to induce cytokine biosynthesis in animals makes the compound of Formula I and conjugates prepared therefrom useful for treating a variety of conditions such as viral diseases and tumors that are responsive to such changes in the immune response. Accordingly, the present invention provides a method of inducing cytokine biosynthesis in an animal by administering to the animal an effective amount of a conjugate prepared from a compound of Formula I and an antigen (in some embodiments, a conjugate having at least one segment represented by Formula II). The present invention further provides a method of vaccinating an animal comprising administering to the animal a conjugate prepared from a compound of Formula I and an antigen (in some embodiments, a conjugate having at least one segment represented by Formula II).

The invention further provides pharmaceutical compositions comprising a pharmaceutically acceptable carrier and an effective amount of a conjugate prepared from a compound of Formula I and an antigen (in some embodiments, a conjugate having at least one segment represented by Formula II).

The terms "comprises" and variations thereof do not have a limiting meaning where these terms appear in the description and claims.

As used herein, "a", "an", "the", "at least one", and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

"Antigen" refers to any substance that may be bound by an antibody in a manner that is immunospecific to some degree for a humoral immune response. "Antigen" as used herein also refers to any substance that may be bound by an antigen-presenting cell for a cell-mediated immune response. An antigen described herein may elicit antigenic activity including, for example, any one or more of the following: generation of antibodies specific to the antigen by B cells, immune cell maturation, cytokine production by immune cells, and generation of antigen-presenting cells that present the antigen. Antigens useful for practicing the present disclosure include those that have very weak activity and/or no therapeutic benefit in the absence of an adjuvant (e.g., such as an IRM compound or a compound of Formula I).

A "conjugate" as used herein is a compound containing two components (e.g., a compound of Formula I and an antigen) covalently linked together.

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

The term "protein" includes proteins and glycoproteins. For proteinaceous antigens, modifications can be made to a particular antigen without rendering the modified antigen unsuitable for use as an antigen. For example, one or more portions of the amino acid sequence of a proteinaceous antigen may be deleted or substituted or additional amino acids may be added, and the proteinaceous antigen can still retain antigenic activity.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION

In one embodiment, the present invention provides a compound of Formula (I):

I

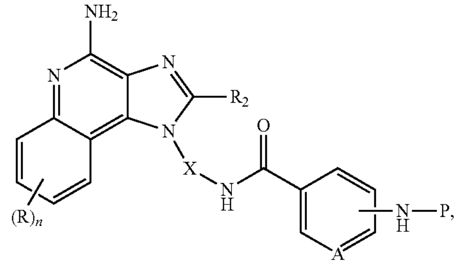

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

P is an amino group, a protected amino group, or $NH_3^+Y^-$, wherein $Y^-$ is a counter anion;

A is CH or N;

R is halogen, hydroxyl, alkyl, haloalkyl, or alkoxy; and n is an integer from 0 to 4;

or a pharmaceutically acceptable salt thereof.

In one embodiment, the present invention provides a compound of Formula (I-A):

I-A

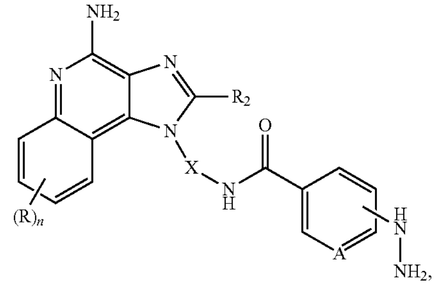

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

A is CH or N;

R is halogen, hydroxyl, alkyl, haloalkyl, or alkoxy; and n is an integer from 0 to 4;

or a salt thereof.

In one embodiment, the present invention provides a conjugate of an antigen, the conjugate having at least one segment represented by Formula (II):

II

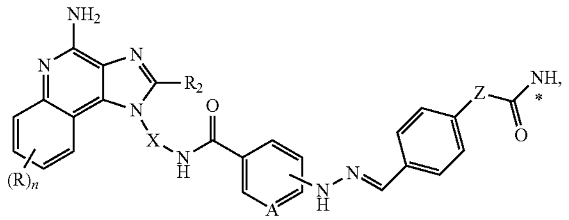

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

A is CH or N;

R is halogen, hydroxyl, alkyl, haloalkyl, or alkoxy;

n is an integer from 0 to 4;

Z is a bond or $—C(O)—NH—(CH_2CH_2O)_p—CH_2CH_2—$, wherein p is in a range from 1 to 50; and the nitrogen atom indicated by N* is covalently bonded to the antigen;

or a pharmaceutically acceptable salt thereof.

As used herein, the terms "alkyl", "alkenyl", "alkynyl", and the prefix "alk-" are inclusive of both straight chain and branched chain groups and of cyclic groups, e.g. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 7 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups include chloromethyl and trifluoromethyl.

An alkylene group with carbon atoms optionally "interrupted" by —O— refers to having carbon atoms on either side of the —O—. An example is $—CH_2—CH_2—O—CH_2—CH_2—$.

An alkylene group with carbon atoms optionally "terminated" by —O— refers to having the —O— on either end of the alkylene group or chain of carbon atoms. Examples include $—O—CH_2—CH_2—CH_2—CH_2—$ and $—CH_2—CH_2—CH_2—CH_2—O—$. In the compounds and conjugates of the present invention, when X is alkylene having up to 8 carbon atoms terminated by —O—, the —O— may be connected to either the nitrogen of the imidazole ring or the nitrogen of the benzamide or nicotinamide group.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, including Formulas I, I-A, and II, each one of the following variables (e.g., X, $R_2$, R, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In some embodiments, X is alkylene having up to 8 carbon atoms optionally interrupted or terminated by —O—.

In some embodiments, X is alkylene having up to 5 carbon atoms optionally interrupted by or terminated by —O—.

In some embodiments, X is $—O—C_{2-8}$ alkylene (e.g., $—O—C_{2-5}$ alkylene). In these embodiments, the —O— is directly attached to the nitrogen of the imidazole ring.

In some embodiments, X is $—O—C_{3-8}$alkylene (e.g., $—O—C_{3-5}$ alkylene). In these embodiments, the —O— is directly attached to the nitrogen of the imidazole ring.

In some embodiments, X is $—C_{1-8}$ alkylene (e.g., $—C_{2-5}$ alkylene).

In some embodiments, X is $—C_{1-8}$ alkylene (e.g., $—C_{2-5}$ alkylene) that is interrupted by —O—.

In some embodiments, X is $—C_{3-8}$ alkylene (e.g., $—C_{3-5}$ alkylene).

In some embodiments, X is —O-butylene (e.g., $—O—CH_2—CH_2—CH_2—CH_2—$). In these embodiments, the —O— is directly attached to the nitrogen of the imidazole ring.

In some embodiments, X is $—CH_2—CH_2—O—CH_2—CH_2—$.

In some embodiments, including any of the above embodiments of Formulas I, I-A, and II where X is defined, $R_2$ is hydrogen, alkyl, alkoxyalkylenyl, alkylaminoalkylenyl, or hydroxyalkylenyl.

In some embodiments, including any of the above embodiments of Formulas I, I-A, and II where X is defined, $R_2$ is hydrogen, alkyl, alkoxyalkylenyl, or hydroxyalkylenyl.

In some embodiments, including any of the above embodiments of Formulas I, I-A, and II where X is defined, $R_2$ is hydrogen, alkyl, or alkoxyalkylenyl.

In some embodiments, including any of the above embodiments of Formulas I, I-A, and II where X is defined, $R_2$ is methyl, ethyl, propyl, butyl, ethoxymethyl, methoxymethyl, ethylaminomethyl, or 2-methoxyethyl.

In some embodiments, including any of the above embodiments of Formulas I, I-A, and II where X is defined, $R_2$ is methyl, ethyl, propyl, butyl, ethoxymethyl, methoxymethyl, or 2-methoxyethyl.

In some embodiments, including any of the above embodiments of Formulas I, I-A, and II where X is defined, $R_2$ is ethyl, butyl, ethoxymethyl, or 2-methoxyethyl.

In some embodiments, including any of the above embodiments of Formulas I, I-A, and II where X is defined, $R_2$ is butyl (e.g., $—CH_2—CH_2—CH_2—CH_3$).

In some embodiments, including any of the above embodiments of Formulas I, I-A, and II where X or $R_2$ is defined, A is CH or N.

In some embodiments, including any of the above embodiments of Formulas I, I-A, and II where X or $R_2$ is defined, A is CH.

In some embodiments, including any of the above embodiments of Formulas I, I-A, and II where X or $R_2$ is defined, A is N.

In some embodiments, including any of the above embodiments of Formulas I, I-A, and II where X, A, or $R_2$ is defined, R is halogen, hydroxyl, alkyl, haloalkyl, or alkoxy.

In some embodiments, including any of the above embodiments of Formulas I, I-A, and II where X, A, or $R_2$ is defined, R is halogen or hydroxyl.

In some embodiments, including any of the above embodiments of Formulas I, I-A, and II where X, A, R, or $R_2$ is defined, n is 1.

In some embodiments, including any of the above embodiments of Formulas I, I-A, and II where X, A, or $R_2$ is defined, n is 0.

In some embodiments, including any of the above embodiments of Formula I where X, A, $R_2$, R, or n is defined, P is an amino group (i.e., $NH_2$), a protected amino group, or $NH_3^+Y^-$, wherein $Y^-$ is a counter anion.

In some embodiments, including any of the above embodiments of Formula I where X, A, $R_2$, R, or n is defined, P is an amino group (i.e., $NH_2$).

In some embodiments, including any of the above embodiments of Formula I where X, A, $R_2$, R, or n is defined, P is $NH_3^+Y^-$ or a protected amino group.

In some embodiments, including any of the above embodiments of Formula I where X, A, $R_2$, R, or n is defined, P is $NH_3^+Y^-$, wherein $Y^-$ is a counter anion. $Y^-$ can be any pharmaceutically acceptable counter anion that does not adversely affect the solubility of the compound of Formula I or interfere with the reaction of the compound of Formula I with an aldehyde-bearing antigen.

In some embodiments, including any of the above embodiments of Formula I where X, A, $R_2$, R, or n is defined, P is $NH_3^+Y^-$, wherein $Y^-$ is a halide (i.e., fluoride, chloride, bromide, and iodide), R'—C(O)—$O^-$, R'—$SO_2$—$O^-$, R"—O—$SO_2$—$O^-$, phosphate, nitrate, sulfate, borate, or tetrafluoroborate, wherein R' and R" are independently alkyl, alkenyl, alkynyl, aryl, arylalkylenyl, heteroaryl, and heteroarylalkylenyl, wherein the alkyl, alkenyl, alkynyl, aryl, arylalkylenyl, heteroaryl, and heteroarylalkylenyl groups can be unsubstituted or substituted by one or more substituents independently selected from the group consisting of alkyl, alkoxy, hydroxyalkyl, haloalkyl, haloalkoxy, halogen, nitro, hydroxyl, cyano, aryl, and aryloxy.

In some embodiments, including any of the above embodiments of Formula I where X, A, $R_2$, R, or n is defined, P is $NH_3^+Cl^-$.

In some embodiments, including any of the above embodiments of Formula I where X, A, $R_2$, R, or n is defined, P is a protected amino group. The protected amino group can be any protected amino group that does not adversely affect the solubility of the compound of Formula I and can be readily removed to allow reaction with an aldehyde-bearing antigen. Exemplary suitable protected amino groups include carbamates and imines In some embodiments, including any of the above embodiments of Formula I where X, A, $R_2$, R, or n is defined, P is a carbamate, which may have the formula —N(H)—C(O)—O—R', wherein R' is alkyl, alkenyl, alkynyl, aryl, arylalkylenyl, heteroaryl, and heteroarylalkylenyl, wherein the alkyl, alkenyl, alkynyl, aryl, arylalkylenyl, heteroaryl, and heteroarylalkylenyl groups can be unsubstituted or substituted by one or more substituents independently selected from the group consisting of alkyl, alkoxy, hydroxyalkyl, haloalkyl, haloalkoxy, halogen, nitro, hydroxyl, cyano, aryl, and aryloxy.

In some embodiments, including any of the above embodiments of Formula I where X, A, $R_2$, R, or n is defined, P is —N(H)—C(O)—O—R', wherein R' is methyl, ethyl, tert-butyl, 9-fluorenylmethyl, 2,2,2-trichloroethyl, 2-trimethylsilylethyl, 2-phenylethyl, 1-adamantyl, or benzyl.

In some embodiments, including any of the above embodiments of Formula I where X, A, $R_2$, R, or n is defined, P is —N(H)—C(O)—O-tert-butyl.

In some embodiments, including any of the above embodiments of Formula I where X, A, $R_2$, R, or n is defined, P is an imine, which may have the formula —N=C(R')$_2$, wherein each R' is independently alkyl, alkenyl, alkynyl, aryl, arylalkylenyl, heteroaryl, and heteroarylalkylenyl, wherein the alkyl, alkenyl, alkynyl, aryl, arylalkylenyl, heteroaryl, and heteroarylalkylenyl groups can be unsubstituted or substituted by one or more substituents independently selected from the group consisting of alkyl, alkoxy, hydroxyalkyl, haloalkyl, haloalkoxy, halogen, nitro, hydroxyl, cyano, aryl, and aryloxy.

In some embodiments, including any of the above embodiments of Formula I where X, A, $R_2$, R, or n is defined, P is —N=C($CH_3$)$_2$.

In some embodiments, including any of the above embodiments of Formulas I where X, A, $R_2$, R, P, or n is defined, the group —NH—P is ortho or meta to A.

In some embodiments, including any of the above embodiments of Formula I where X, A, $R_2$, R, P, or n is defined, the group —NH—P is ortho to A.

In some embodiments, including any of the above embodiments of Formula I where X, A, $R_2$, R, P, or n is defined, the group —NH—P is meta to A.

In some embodiments, including any of the above embodiments of Formula I-A where X, A, $R_2$, R, or n is defined, the group —NH—$NH_2$ is ortho or meta to A.

In some embodiments, including any of the above embodiments of Formula I-A where X, A, $R_2$, R, or n is defined, the group —NH—$NH_2$ is ortho to A.

In some embodiments, including any of the above embodiments of Formula I-A where X, A, $R_2$, R, or n is defined, the group —NH—$NH_2$ is meta to A.

In some embodiments, including any of the above embodiments of Formula II where X, A, $R_2$, R, or n is defined, the group —NH—N=CH— is ortho or meta to A.

In some embodiments, including any of the above embodiments of Formula II where X, A, $R_2$, R, or n is defined, the group —NH—N=CH— is ortho to A.

In some embodiments, including any of the above embodiments of Formula II where X, A, $R_2$, R, or n is defined, the group —NH—N=CH— is meta to A.

In some embodiments, including any of the above embodiments of Formula II where X, A, $R_2$, R, n, or the position of the group —NH—N=CH— is defined, Z is a bond. In embodiments where Z is a bond, it should be understood that Z is absent, and the segment represented by Formula II can also be written:

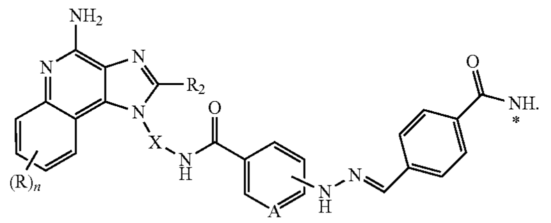

In some embodiments, including any of the above embodiments of Formula II where X, A, $R_2$, R, n, or the position of the group —NH—N=CH— is defined, Z is —C(O)—NH—($CH_2CH_2O$)$_p$—$CH_2CH_2$—. In these embodiments, it should be understood that the carbonyl group is attached to the aromatic ring, and the segment represented by Formula II can also be written:

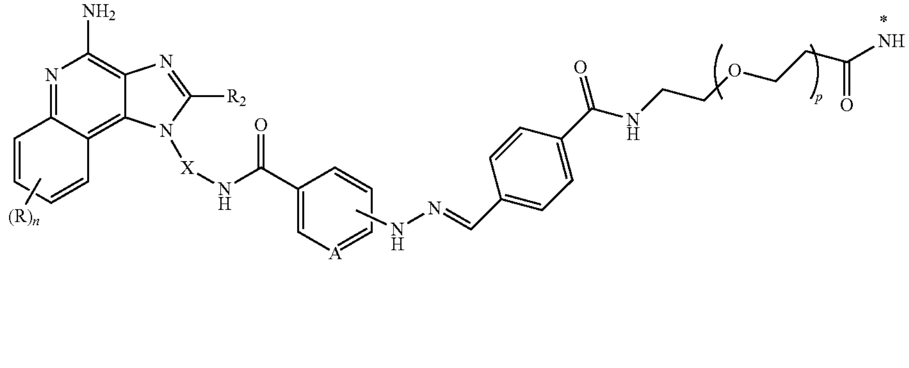

In some of these embodiments, p is in a range from 1 to 50. In other embodiments, p is in a range from 2 to 50, 1 to 40, 2 to 40, 1 to 30, 2 to 30, 2 to 24, 2 to 16, 2 to 12, 4 to 24, 4 to 16, or 4 to 12.

In some embodiments of Formulas I, I-A, and II, n is 0, X is —O—$C_{3-5}$alkylene, and $R_2$ is methyl, ethyl, propyl, butyl, ethoxymethyl, methoxymethyl, or 2-methoxyethyl.

In some embodiments of Formulas I, I-A, and II, n is 0, X is —O-butylene, and $R_2$ is butyl. In some embodiments, the compound of Formula I is N-(4-{[4-amino-2-butyl-1H-imidazo[4,5-c]quinolin-1-yl]oxy}butyl)-6-hydazinonicotinamide

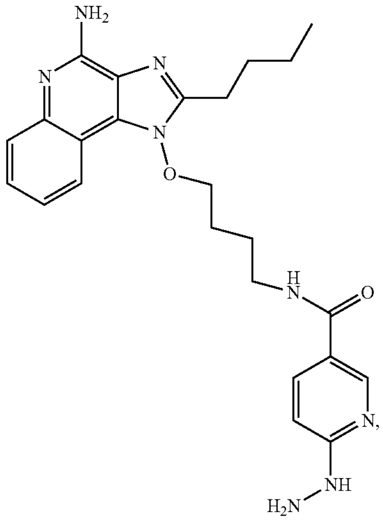 [SMILES: CCCCc1nc2c(N)nc3ccccc3c2n1OCCCCNC(=O)c1ccc(NN)nc1]

or a pharmaceutically acceptable salt thereof.

In some embodiments, the compound of Formula I is N-(4-{[4-amino-2-butyl-1H-imidazo[4,5-c]quinolin-1-yl]oxy}butyl)-6-(N'-isopropylidenehydrazino)nicotinamide:

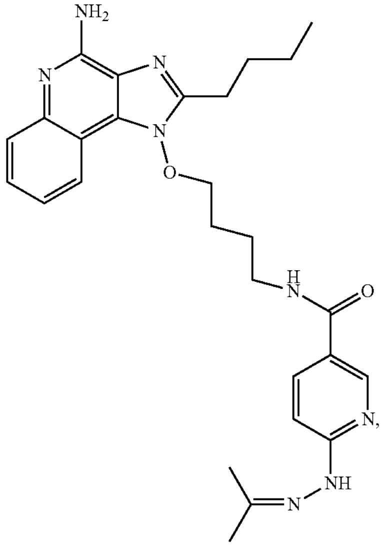

or a pharmaceutically acceptable salt thereof.

In some embodiments, the compound of Formula I is N-(4-{[4-amino-2-butyl-1H-imidazo[4,5-c]quinolin-1-yl]oxy}butyl)-4-(N'-isopropylidenehydrazino)benzamide:

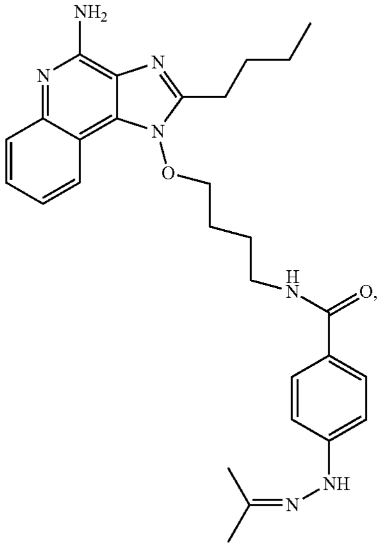 [SMILES: CCCCc1nc2c(N)nc3ccccc3c2n1OCCCCNC(=O)c1ccc(NN=C(C)C)nc1]

or a pharmaceutically acceptable salt thereof.

In some embodiments, the compound of Formula I is N-(4-{[4-amino-2-butyl-1H-imidazo[4,5-c]quinolin-1-yl]oxy}butyl)-4-hydazinobenzamide:

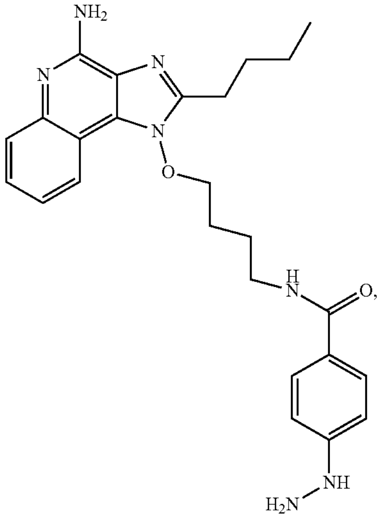

or a pharmaceutically acceptable salt thereof.

As defined above, "antigen" refers to any substance that may be bound in a manner that is immunospecific to some degree and may elicit a humoral immune response, a cell-mediated response, or both. Exemplary antigens include peptide, polypeptide, protein, glycoprotein, lipid, glycolipid, polysaccharide, carbohydrate, polynucleotide, prions, oligonucleotide (e.g., CpG), DNA, virus, bacteria, fungus, parasite, toxin, or toxoid).

In some embodiments, including any of the above embodiments of Formula II where X, A, $R_2$, R, n, p, or the position of the group —NH—N═CH— is defined, the antigen is a protein.

In some embodiments, including any of the above embodiments of Formula II where X, A, $R_2$, R, n, p, or the position of the group —NH—N═CH— is defined, the antigen is a lipid.

In some embodiments, including any of the above embodiments of Formula II where X, A, $R_2$, R, n, p, or the position of the group —NH—N═CH— is defined, the antigen is a vaccine.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

In Reaction Scheme I, intermediate compounds useful for practicing the present invention are described. In step (1) of Reaction Scheme I, the hydrazinobenzoic acid or hydrazinonicotinic acid compound of Formula IV is reacted with acetone at ambient temperature to provide the hydrazone substituted compound of Formula V. The starting hydrazine substituted compounds of Formula IV are 4-hydrazinobenzoic acid (IV where A=CH) and 6-hydrazinonicotinic acid (IV where A=N). These compounds can be prepared using the reaction conditions described by Lagisetty, P.; Vilekar, P.; and Awasthi, V. *Biorganic and Medicinal Chemistry Letters,* 19, pp. 4764-4767 (2009), or Pegurier, C.; Collart, P.; Danhaive, P.; Defays, S.; Gillard, M.; Gilson, F.; Kogej, T.; Pasau, P.; Van Houtvin, N.; Van Thuyne, M.; Van Keulen, B. *Bioorganic and Medicinal Chemistry Letters,* 17, pp. 4228-4231 (2007), or Int. Pat. App. Pub. No. WO2006071940 (Flynn et al.).

In step (2) of Reaction Scheme I, the compound of Formula V is reacted at ambient temperature with N-hydroxysuccinimide and a standard coupling reagent such as 1,3-dicyclohexylcarbodiimide (DCC) or 1-[3-(dimethylamino)propyl]-3-ethylcarbodiimide (EDC) in a suitable solvent such as dichloromethane or pyridine. The product of Formula VI can be isolated using conventional means.

In step (3) of Reaction Scheme I, the hydrazinobenzoic acid or hydrazinonicotinic acid compound of Formula VII is reacted with acetone at ambient temperature to provide the hydrazone substituted compound of Formula VIII. The starting hydrazine substituted compounds of Formula VII are 3-hydrazinobenzoic acid (VII where A=CH) and 5-hydrazinonicotinic acid (VII where A=N). These compounds can be prepared according to the procedures in the references provided to prepare the compounds of Formula IV.

In step (4) of Reaction Scheme I, the compound of Formula VIII is reacted at ambient temperature with N-hydroxysuccinimide using, for example, the conditions described above for step (2).

Reaction Scheme I

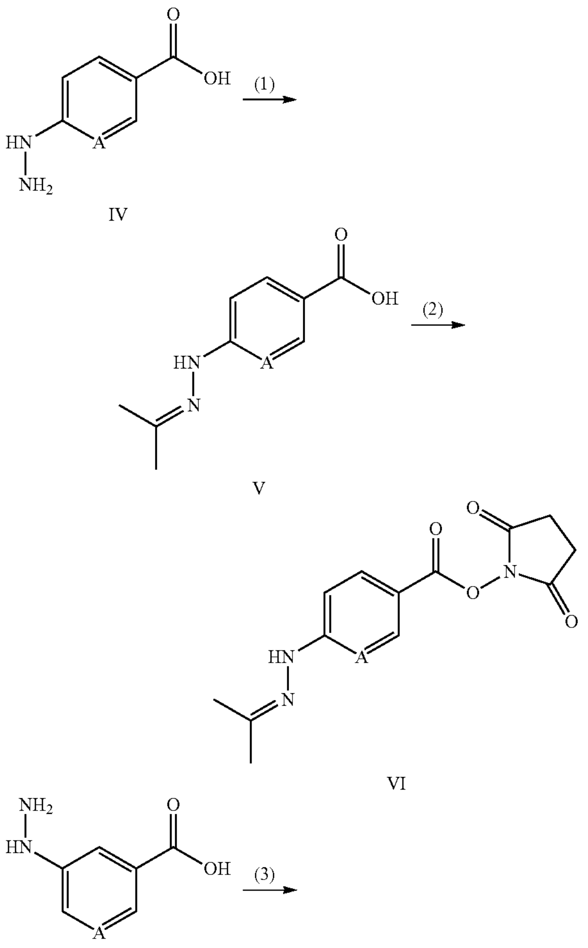

IV

V

VI

VII

-continued

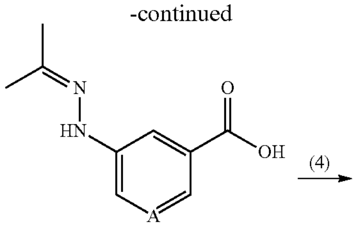

VIII

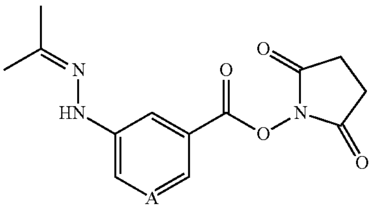

IX

Compounds of the invention can be prepared according to Reaction Scheme II wherein R, $R_2$, A, and n are as defined above, and X' is alkylene having up to 8 carbon atoms.

In step (1) of Reaction Scheme II, a 4-chloro-3-nitroquinoline of Formula X is reduced to provide a 3-amino-4-chloroquinoline of Formula XI. The reduction can be carried out using a conventional heterogeneous hydrogenation catalyst such as platinum on carbon or palladium on carbon. For some compounds of Formula X, for example, compounds in which R is halogen, a platinum catalyst is preferred. The reaction can be carried out using a Parr apparatus in a suitable solvent such as toluene and/or isopropanol. The product can be isolated by conventional methods. Many compounds of Formula X are known or can be prepared using known synthetic methods, see for example, U.S. Pat. No. 4,689,338 (Gerster); U.S. Pat. No. 5,175,296 (Gerster); U.S. Pat. No. 5,367,076 (Gerster); and U.S. Pat. No. 5,389,640 (Gerster et al.); and the documents cited therein. Some compounds of Formula XI are known. For example, 3-amino-4-chloroquinoline, 3-amino-4,5-dichloroquinoline, and 3-amino-4,7-dichloroquinoline have been prepared by Surrey et al. *Journal of the American Chemical Society,* 73, pp. 2413-2416 (1951).

Alternatively, the reduction step (1) can be carried out using a one- or two-phase sodium dithionate reduction. The reaction is carried out using the conditions described by Park, K. K.; Oh, C. H.; and Joung, W. K. *Tetrahedron Letters,* 34, pp. 7445-7446 (1993) by adding sodium dithionate to a compound of Formula X in a mixture of dichloromethane and water at ambient temperature in the presence of potassium carbonate and ethyl viologen dibromide, ethyl viologen diiodide, or 1,1'-di-n-octyl-4,4'-bipyridinium dibromide. The product can be isolated using conventional methods.

In step (2) of Reaction Scheme II, a 3-amino-4-chloroquinoline of Formula XI is reacted with an acyl halide of Formula $R_2C(O)C_1$ or $R_2C(O)Br$ to provide an N-(4-chloroquinolin-3-yl) amide of Formula XII. The acyl halide is added to a solution of a compound of Formula XI in a suitable solvent such as dichloromethane in the presence of a base such as triethylamine, pyridine, or 4-dimethylaminopyridine. The reaction can be run at a reduced temperature, for example, 0° C., or at ambient temperature. The product can be isolated by conventional methods such as recrystallization.

In step (3) of Reaction Scheme II, an N-(4-chloroquinolin-3-yl) amide of Formula XII is reacted with a hydroxylamine of Formula CBZ-NH—X'—$ONH_2$ and cyclized to provide a 1H-imidazo[4,5-c]quinoline of Formula XIII. CBZ is a common chemical abbreviation for the carboxybenzyl group. The CBZ-NH—X'—$ONH_2$ is added to a solution of a compound of Formula XII in an alcoholic solvent. The reaction can be carried out at an elevated temperature, for example, at reflux temperature in isopropanol. A base such as triethylamine can also be added to the reaction. The product can be isolated by conventional methods such as recrystallization.

The CBZ-NH—X'—$ONH_2$ compound used in step (3) of Reaction Scheme II can be prepared by reacting an aminoalkylalcohol of the Formula $H_2N$—X'—OH with benzylchloroformate to provide a compound of Formula CBZ-NH—X'—OH. The benzylchloroformate is added to a solution of Formula $H_2N$—X'—OH in a suitable solvent such as dichloromethane in the presence of a base such as pyridine. The reaction can initially be run at a reduced temperature, for example 0° C., then slowly warmed to ambient temperature. The product can be isolated by conventional methods such as recrystallization. The compound of Formula CBZ-NH—X'—OH is further reacted using Mitsunobu Reaction conditions to provide a compound of Formula CBZ-NH—X'—$ONH_2$. N-hydroxyphthalimide, the compound of Formula CBZ-NH—X'—OH, and triphenylphosphine are combined in a suitable solvent such as dichloromethane and chilled to 0° C. Diisopropylazodicarboxylate (DIAD) is slowly added and the reaction is warmed to ambient temperature. If needed, the reaction can be carried out at an elevated temperature such as 60° C. Following concentration under reduced pressure, the phthalimide protecting group is removed by treating with hydrazine (aqueous solution) in a suitable solvent such as ethanol. The product of Formula CBZ-NH—X'—$ONH_2$ can be isolated by conventional methods such as recrystallization.

In step (4) of Reaction Scheme II, a 1H-imidazo[4,5-c]quinoline of Formula XIII is carried through three transformations to provide a 1H-imidazo[4,5-c]quinoline-4-amine of Formula XIV. First, a compound of Formula XIII is oxidized using a conventional oxidizing agent that is capable of forming the N-oxide of the nitrogen atom in the pyridine ring. The reaction is carried out by treating a solution of the compound of Formula XIII in a suitable solvent such as chloroform or dichloromethane with 3-chloroperoxybenzoic acid. The N-oxide reaction product may optionally be isolated, or the second transformation may be carried out in the same reaction vessel with the in-situ formed N-oxide. In the second transformation, the N-oxide product is aminated by activation of the N-oxide with a suitable activating agent followed by amination with a suitable aminating agent. Suitable activating agents include alkyl- or arylsulfonyl chlorides (e.g., benzenesulfonyl chloride, methanesulfonyl chloride, and p-toluenesulfonyl chloride). Arylsulfonyl chlorides (e.g., p-toluenesulfonyl chloride) are useful in some embodiments. Suitable aminating agents include ammonia (e.g. in the form of ammonium hydroxide) and ammonium salts (e.g., ammonium carbonate, ammonium bicarbonate, ammonium phosphate). The reaction can be carried out by dissolving the N-oxide of a compound of Formula XIII in a suitable solvent such as dichloromethane, 1,2-dichloroethane, or chloroform and adding ammonium hydroxide followed by the arylsulfonyl chloride. The reaction may optionally be carried out with heating. Optionally the reaction can be carried out in a sealed pressure vessel at an elevated temperature (85-100° C.). In the third transformation, the CBZ protecting group is removed under acidic conditions (e.g. concentrated hydrochloric acid at elevated temperature) to provide the compound of Formula XIV. A compound of Formula XIV can be isolated by conventional methods either as the free base or as an acid salt (e.g. maleate or fumarate salt)

In step (5) of Reaction Scheme II, a compound of Formula XIV is reacted with a compound of Formula V (from Reaction Scheme I where A=CH or N) to provide a compound of Formula XV. The reaction can be conducted at ambient temperature in a solvent such as dichloromethane, pyridine, or 1-butanol with a standard coupling reagent such as 1,3-dicyclohexylcarbodiimide (DCC) or 1-[3-(dimethylamino)propyl]3-ethylcarbodiimide (EDC). A compound of Formula XV can be isolated using conventional methods. As an alternative method for step (5) of Reaction Scheme II, a compound of Formula XIV is reacted with a compound of Formula VI (from Reaction Scheme I where A=CH or N) to provide a compound of Formula XV. The compound of Formula XIV can be dissolved in a suitable alcoholic solvent such a 1-butanol and the compound of Formula VI can be slowly added at ambient temperature.

In step (6) of Reaction Scheme II, the acetamine protecting group is removed under acidic conditions to provide the compound of Formula XVI. The reaction can be conducted in hydrochloric acid at ambient or elevated temperature (e.g. 60° C.). A product of Formula XVI can be isolated, for example, as a hydrochloride salt by lyophilization.

In step (7) of Reaction Scheme II, a compound of Formula XIV is reacted with a compound of either Formula VIII or Formula IX (from Reaction Scheme I where A=CH or N) according to the corresponding procedure described in step (5) to provide a compound of Formula XVII.

In step (8) of Reaction Scheme II, the acetamine protecting group is removed under acidic conditions to provide the compound of Formula XVIII. The reaction can be conducted according to the procedure described in step (6).

Reaction Scheme II

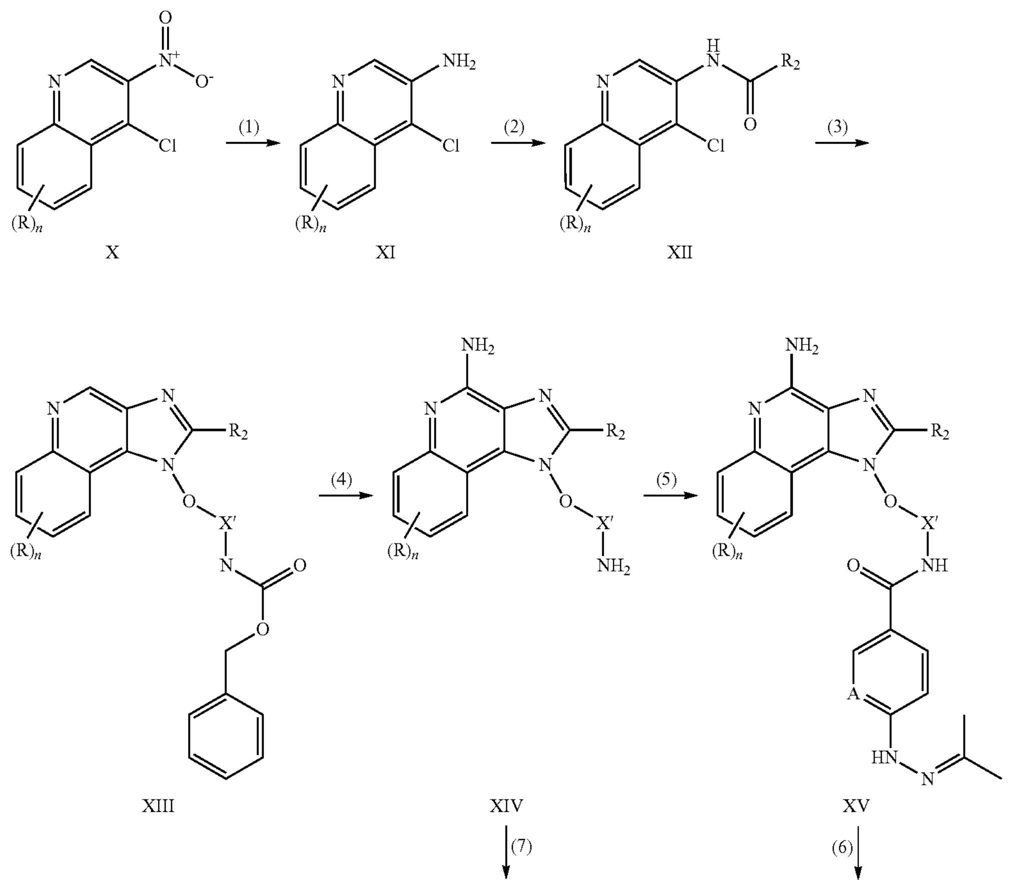

X XI XII XIII XIV XV

-continued

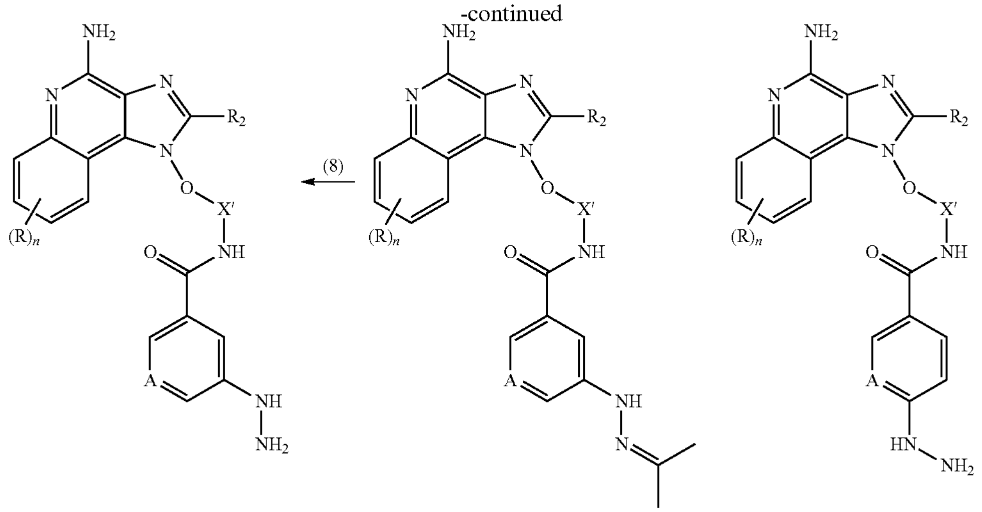

XVIII XVII XVI

Compounds of the invention can be prepared according to Reaction Scheme III wherein R, $R_2$, A and n are as defined above, and X' is alkylene having up to 8 carbon atoms.

In step (1) of Reaction Scheme III, a 4-chloro-3-nitroquinoline of Formula X is treated with an amine of Formula HO—X'—$NH_2$ to provide a compound of Formula XIX. Several amines of Formula HO—X'—$NH_2$ are commercially available and others can be prepared by known synthetic methods. The reaction is carried out by adding the amine of Formula HO—X'—$NH_2$ to a solution of the 4-chloro-3-nitroquinoline of Formula X in a suitable solvent such as dichloromethane in the presence of a tertiary amine such as triethylamine. The reaction can be carried out at ambient temperature or at a sub-ambient temperature such as, for example, 0° C. The reaction product can be isolated using conventional methods.

In step (2) of Reaction Scheme III, a compound of Formula XIX is reduced to provide a diamine of Formula XX. The reduction can be carried out, for example, using methods described in step (1) of Reaction Scheme II.

In step (3) of Reaction Scheme III, a diamine of Formula XX is reacted with a carboxylic acid equivalent to provide a 1H-imidazo[4,5-c]quinoline of Formula XXI. Suitable carboxylic acid equivalents include orthoesters of the Formula $R_2C(O\text{-alkyl})_3$, 1,1-dialkoxyalkyl alkanoates of the Formula $R_2C(O\text{-alkyl})_2(O—C(O)\text{-alkyl})$, and acid chlorides of the Formula $R_2C(O)Cl$. The selection of the carboxylic acid equivalent is determined by the desired substituent at $R_2$. For example, triethylorthoformate will provide a compound where $R_2$ is hydrogen, and trimethyl orthobutyrate will provide a compound where $R_2$ is a propyl group.

Step (3) can be carried out by adding the carboxylic acid equivalent to a diamine of Formula XX in a suitable solvent such as toluene or xylenes. Optionally, catalytic pyridine hydrochloride can be added. The reaction is typically carried out at a temperature high enough to drive off alcohol or water formed during the reaction. Conveniently, a Dean-Stark trap can be used to collect the volatiles. The 1H-imidazo[4,5-c]quinoline product of Formula XXI can be isolated and optionally purified using conventional techniques. Alternatively, step (3) of Reaction Scheme III can be carried out in two steps when an acid chloride of the Formula $R_2C(O)Cl$ is used as the carboxylic acid equivalent. Part (i) of step (3) can be carried out by adding the acid chloride to a solution of a diamine of Formula XX in a suitable solvent such as dichloromethane or acetonitrile. Optionally, a tertiary amine such as triethylamine, pyridine, or 4-dimethylaminopyridine can be added. The reaction can be carried out at ambient temperature. The amide product can be isolated and optionally purified using conventional techniques. Part (ii) of step (3) involves heating the amide prepared in part (i) in the presence of base to provide 1H-imidazo[4,5-c]quinoline of Formula XXI. The reaction can be carried out in a suitable solvent such as ethanol in the presence of a base such as sodium hydroxide or aqueous potassium carbonate at elevated temperature. The product of Formula XXI can be isolated using conventional methods.

Several compounds of Formula XXI, wherein n is 0 are known and have been prepared by other related routes; see for example, U.S. Pat. No. 4,689,338 (Gerster), U.S. Pat. No. 5,605,899 (Gerster et al.), and U.S. Pat. No. 5,175,296 (Gerster).

In step (4) of reaction Scheme III, a hydroxyl-substituted compound of Formula XXI is treated with N-hydroxyphthalimide under Mitsunobu reaction conditions to provide an N-phthalimide-protected hydroxylamine of Formula XXII. The reaction can be carried out by adding triphenylphosphine and N-hydroxyphthalimide to a solution of the alcohol of Formula XXI in a suitable solvent such as tetrahydrofuran or N,N-dimethylformamide and then slowly adding diisopropylazodicarboxylate (DIAD). The reaction can be carried out at ambient temperature or at an elevated temperature such as 60° C. The product can be isolated using conventional methods.

In steps (5) and (6) of Reaction Scheme III, an N-phthalimde-protected hydroxylamine of Formula XXII is oxidized to provide a 1H-imidazo[4,5-c]quinoline-5N-oxide of Formula XXIII using a conventional oxidizing agent capable of forming N-oxides, and then the 1H-imidazo[4,5-c]quinoline-5N-oxide of Formula XXIII is aminated to provide a 1H-imidazo[4,5-c]quinolin-4-amine of Formula XXIV. The reactions can be carried out using the conditions described in the first and second transformations in step (4) of Reaction Scheme II. Under these conditions, the N-phtalimide protecting group is removed to provide the 1H-imidazo[4,5-c]quinoline-4-amine of Formula XXIV. Compounds of Formula XXIV are known and other methods of their preparation have been described; see for example, U.S. Pat. No. 7,648,997 (Kshirsagar, et al.).

In step (7) of Reaction Scheme III, a compound of Formula XXIV is reacted with a compound of Formula V or VI (from Reaction Scheme I where A=CH or N) to provide a compound of Formula XXV. The reaction can be carried out according to the corresponding method described in step (5) of Reaction Scheme II.

In step (9) of Reaction Scheme III, a compound of Formula XXIV is reacted with a compound of either Formula VIII or Formula IX (from Reaction Scheme I where A=CH or N) according to the corresponding procedure described in step (5) of Reaction Scheme II to provide a compound of Formula XXVII.

In steps (8) and (10) of Reaction Scheme III, the acetamine protecting group is removed under acidic conditions to provide the compound of Formula XXVI and XXVIII, respectively, as described in step (6) of Reaction Scheme II.

Reaction Scheme III

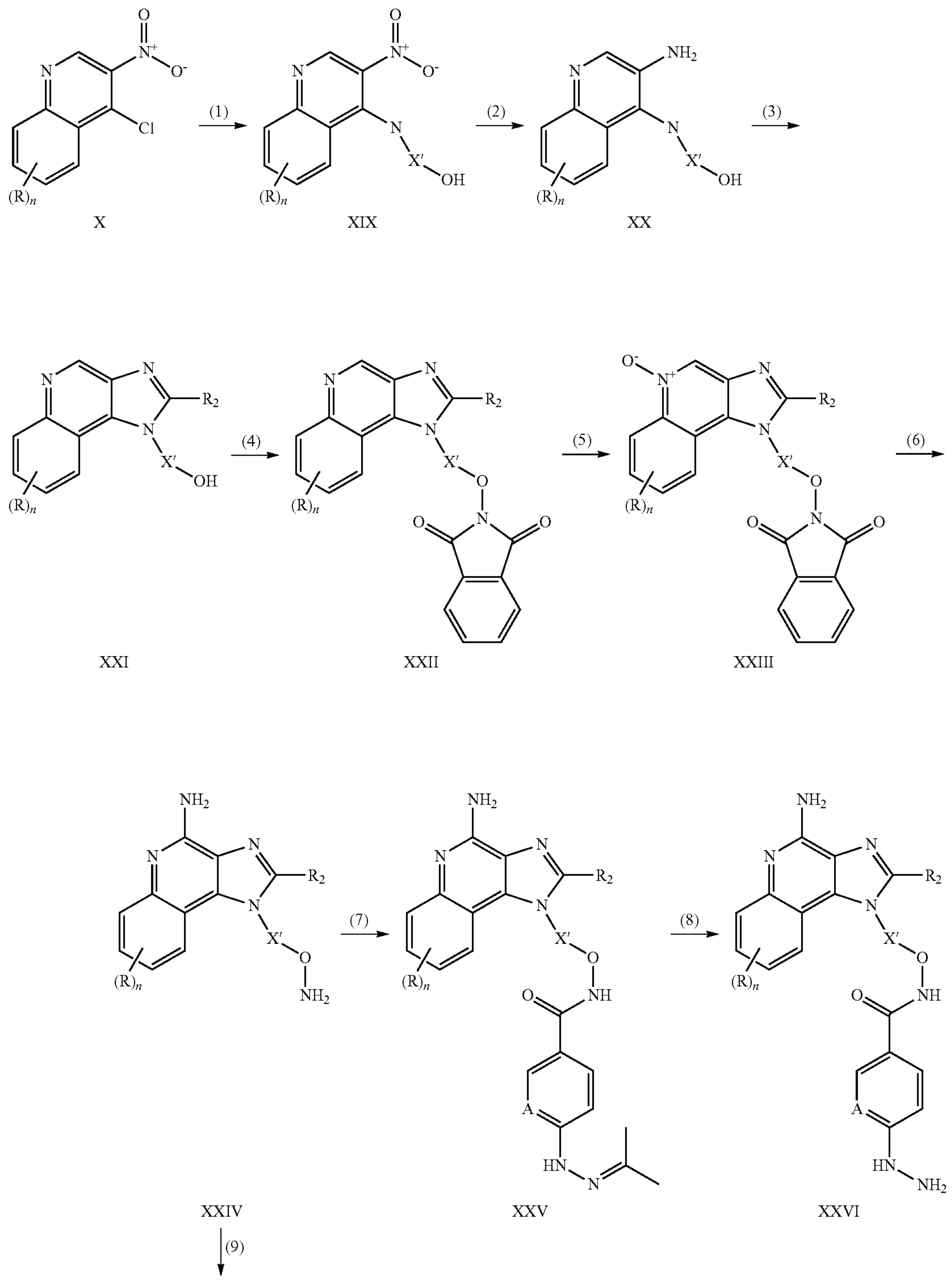

X XIX XX

XXI XXII XXIII

XXIV XXV XXVI

-continued

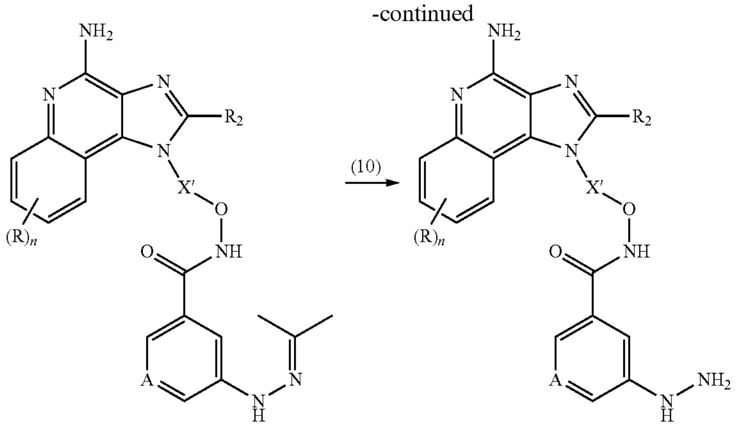

XXVII XXVIII

Compounds of the invention can be prepared according to Reaction Scheme IV wherein R, $R_2$, A and n are defined as above, BOC is tert-butoxycarbonyl, and Y and Z are alkylene groups having a total of up to 8 carbon atoms.

In step (1) of Reaction Scheme IV the amino group of an aminoalcohol of Formula XXIX is protected with a tert-butoxycarbonyl group (BOC) to provide a compound of Formula XXX. A solution of the aminoalcohol in tetrahydrofuran can be treated with di-tert-butyl dicarbonate in the presence of a base such as sodium hydroxide. Many aminoalcohols of Formula XXIX are commercially available, and others can be prepared using known synthetic methods.

In step (2) of Reaction Scheme IV a protected aminoalcohol of Formula XXX is converted to an iodide of Formula XXXI. Iodine can be added to a solution of triphenylphosphine and imidazole in dichloromethane and then a solution of the protected aminoalcohol XXX in dichloromethane can be added. The reaction can be carried out at ambient temperature. The compound of Formula XXXI can be isolated using conventional methods.

In step (3) of Reaction Scheme IV a 1H-imidazo[4,5-c]quinolin-1-yl alcohol of Formula XXXII is alkylated with an iodide of Formula XXXI to provide a 1H-imidazo[4,5-c]quinolin-1-yl ether of Formula XXXIII. The 1H-imidazo[4,5-c]quinolin-1-yl alcohol of Formula XXXII represents a subset of the compounds represented by Formula XXI in Reaction Scheme III. The compound of Formula XXXII can be prepared using the procedure described for the synthesis of the compound of Formula XXI in Reaction Scheme III. In step (3), the alcohol of Formula XXXII can be reacted with sodium hydride in a suitable solvent such as N,N-dimethylformamide to form an alkoxide. The iodide is added to the alkoxide solution at ambient temperature and then stirred at an elevated temperature (approximately 100° C.).

In step (4) of Reaction Scheme IV a 1H-imidazo[4,5-c]quinolin-1-yl ether of Formula XXXIII is oxidized to provide a 1H-imidazo[4,5-c]quinoline-5N-oxide of Formula XXXIV. In step (5) of Reaction Scheme IV a 1H-imidazo[4,5-c]quinoline-5N-oxide of Formula XXXIV is aminated to provide a 1H-imidazo[4,5-c]quinolin-4-amine of Formula XXXV. The reactions can be carried out using the conditions described in the first and second transformations in step (4) of Reaction Scheme II.

In step (6) of Reaction Scheme IV the BOC protecting group is removed by hydrolysis under acidic conditions to provide a 1H-imidazo[4,5-c]quinoline-4-amine of Formula XXXVI. The compound of Formula XXXV may be treated with hydrochloric acid in ethanol at ambient temperature or with gentle heating. Compounds of Formula XXXVI, wherein n is 0 are known and methods of preparation and isolation have been described; see for example, U.S. Pat. No. 6,660,747 (Crooks, et al.).

In step (7) of Reaction Scheme IV, a compound of Formula XXXVI is reacted with a compound of Formula V or VI (from Reaction Scheme I where A=CH or N) to provide a compound of Formula XXXVII. The reaction can be carried out according to the corresponding method described in step (5) of Reaction Scheme II.

In step (9) of Reaction Scheme IV, a compound of Formula XXXVI is reacted with a compound of either Formula VIII or Formula IX (from Reaction Scheme I where A=CH or N) according to the corresponding procedure described in step (5) of Reaction Scheme II to provide a compound of Formula XXXIX.

In steps (8) and (10) of Reaction Scheme IV, the acetamine protecting group is removed under acidic conditions to provide the compound of Formula XXXVIII or XL, respectively. The reaction can be conducted in hydrochloric acid at ambient or elevated temperature (e.g. 60° C.). A product of Formula XXXVIII or XL can be isolated as a hydrochloride salt by lyophilization.

Reaction Scheme IV
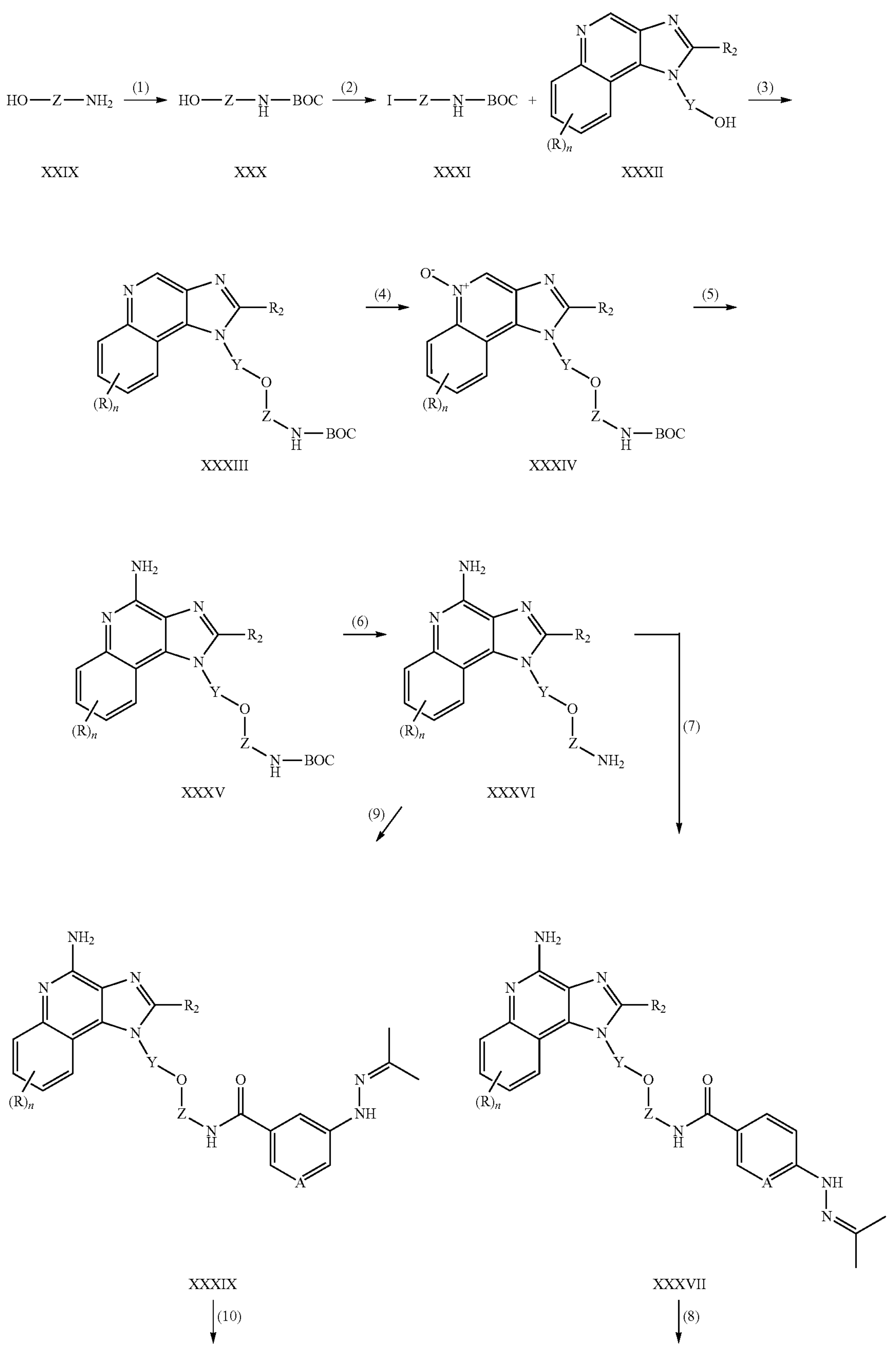
XXIX XXX XXXI XXXII
XXXIII XXXIV
XXXV XXXVI
XXXIX XXXVII -continued

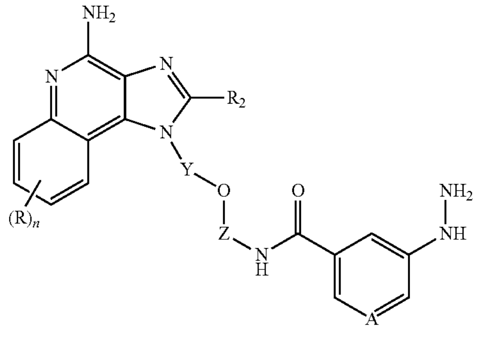

XXXIV

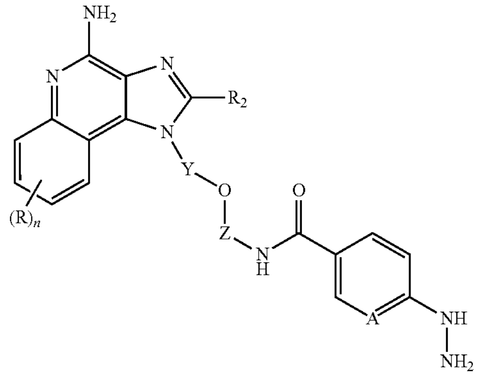

XXXVIII

Compounds of the invention can also be made using modifications of Reaction Schemes I to IV that would be apparent to a person skilled in the art. For example, compounds of Formula I with an X group containing up to 8 carbon atoms can be made using a modification of Reaction Scheme IV starting with a compound of formula XXXVI where —Y—O—Z— is replaced with $C_{1-8}$ alkylene. Such starting compounds can be made using methods described in U.S. Pat. No. 6,069,149 (Nanba). In another example, compounds of Formula I with an alkylaminoalkylenyl group can be prepared using a modification of Reaction Schemes II to IV using the methods described in, fore example, U.S. Pat. No. 5,389,640 (Gerster et al.). Compounds of the invention can also be prepared using the synthetic routes described in the EXAMPLES below.

Preparation of the Conjugates

Compounds of Formula I or I-A may be reacted with an aldehyde-bearing antigen to provide conjugates of the invention. Accordingly, conjugates of the present invention are typically reaction products of the compound or salt of Formula I or I-A and an aldehyde-bearing antigen. These reaction products are typically hydrazonobenzamide or hydrazononicotinamide 1H-imidazo[4,5-c]quinolin-4-amines.

Aldehyde-bearing antigens can be prepared according to a variety of methods. In some cases, an antigen can be reacted with a heterobifunctional linking compound bearing an aldehyde functional group and a second reactive functional group. In such cases, the antigen typically has a reactive functional group that allows a reaction with a heterobifunctional linking compound (e.g., at the second reactive functional group). For example, an antigen may have one or more (e.g., typically multiple) terminal amino groups from lysine residues that may be reactive, for example, with a carboxylic acid or derivatives thereof on the heterobifunctional linking compound. It will be appreciated by those of skill in the art that in biomolecules such as proteins that contain multiple amino groups (i.e., lysines), as many amino groups as desired may be reacted with heterobifunctional linking compounds. The degree of modification can be controlled by the number of mole equivalents of linking compounds used.

In some embodiments, the heterobifunctional linking compound is aromatic. As a specific example, amino-functional antigens can be reacted with succinimidyl 4-formylbenzoate (SFB) to form an amide bond and to provide an aldehyde functional group covalently linked to the antigen through the aromatic ring. The reaction can be carried out in an appropriate buffered solution (e.g., in a phosphate buffer at a pH in a range from 7.2 to 7.5). SFB can be dissolved in an appropriate polar solvent (e.g., DMSO or DMF) and combined with the buffered solution containing the antigen. The reaction can conveniently be carried out at room temperature.

In some embodiments, the heterobifunctional linking compound is aromatic and includes a poly(ethyleneoxy) segment. In some of these embodiments, the heterobifunctional linking compound is

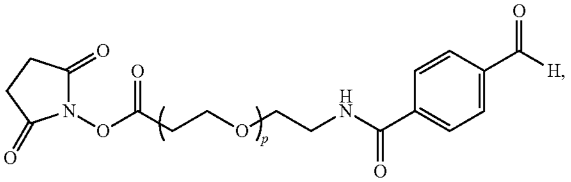

wherein p is as defined above in any of its embodiments. Such compounds may be prepared for example, by reacting a carboxy-PEG-amine compound such as those available from Thermo Scientific, Rockford, Ill., with N-succinimidyl-4-formyl benzoate. Subsequently, the carboxylic acid group can be converted to an activated ester, for example, by reaction with N,N,N',N'-tetramethyl-O—(N-succinimidyl)uronium tetrafluoroborate (TSTU). The reaction of the heterobifunctional linking compound with the antigen can be carried out in an appropriate buffered solution (e.g., in a phosphate buffer at a pH in a range from 7.2 to 7.5). The heterobifunctional linking compound can be dissolved in an appropriate polar solvent (e.g., DMSO or DMF) and combined with the buffered solution containing the antigen. The reaction can conveniently be carried out at room temperature. For additional information regarding such heterobifunctional linking compounds, see co-pending U.S. Pat. Appl. Ser. No. 61/493,143, filed on Jun. 3, 2011, the disclosure of which is incorporated herein by reference in its entirety.

In other embodiments, the antigen may not require a heterobinfunctional linking compound. For example, the antigen may have a functional group that can readily be transformed to an aldehyde group. For example, a primary hydroxyl group on a carbohydrate of a glycoprotein or glycolipid can be readily oxidized to an aldehyde.

In some embodiments, the present invention provides a composition comprising the compound or salt of Formula I, an aldehyde-bearing antigen, and a pharmaceutically acceptable carrier. Conjugates of the invention may be prepared in such compositions. In some embodiments of making a conjugate according to the present invention, the compound or salt of Formula I or I-A can be dissolved in an appropriate polar solvent (e.g., DMSO, DMF) and combined with an appropriate buffered solution of the aldehyde-bearing antigen. If a compound of Formula I is used wherein P is an acid-labile protected amino group, for example, an acidic buffered solution (e.g., with a pH in a range from 4.7 to 6.2) can effect the deprotection of the amino group and allow reaction with the aldehyde-bearing antigen at the same time. The reaction is typically carried out at room temperature. Accordingly, in some embodiments, the present invention provides a method of making a conjugate, the method comprising combining a compound or salt of Formula I, wherein P is a protected amino group; an aldehyde-bearing antigen, and a carrier under conditions where the protected amino group is deprotected and the conjugate is formed.

When an aromatic, aldehyde-bearing heterobifunctional linking compound is used to prepare the aldehyde-bearing antigen (e.g., when amino-functional antigens are reacted with succinimidyl 4-formylbenzoate (SFB) to form an amide bond and to provide an aldehyde functional group covalently linked to the antigen), the reaction of the aromatic aldehyde group with a compound of Formula I can conveniently be followed using a UV spectrophotometric assay. The bis-aromatic hydrazone bond that is formed provides a distinctive chromophore with a maximal absorbance a 354 nm and a molar extinction coefficient equal to 29,000. The number of moles of a compound of Formula I incorporated into antigen can be calculated by dividing the measured absorbance of the conjugate at 354 nm by the molar extinction coefficient of 29,000 as demonstrated in the Examples, below.

To promote solubility and stability in the reaction to provide conjugates disclosed herein, various additives may be useful in the reaction mixture depending on the properties of the selected antigen or protein. For example, glycerol and/or surfactants (e.g., polysorbate 80) can be useful for promoting solubility and stability. Also, providing a poly(ethyleneoxy) segment in the conjugate can be useful for promoting solubility and stability. In some of these embodiments, Z is $—C(O)—NH—(CH_2CH_2O)_p—CH_2CH_2—$, wherein p is as defined in any of the above embodiments. To promote reaction efficiency, catalysts (e.g., aniline) may be added in effective amounts (e.g., up to 200 mM). Catalysts may be useful, for example, for facilitating the reaction when glycerol and/or surfactants are added to the reaction mixture.

In some embodiments, the antigen is a protein. Exemplary proteins that may be useful antigens in conjugates of the invention include hemagglutinin from H1N1 PR8, hepatitis B surface antigen, *Leishmania* antigen, respiratory syncytial virus secretory protein F, malaria surface antigen, prostatic alkaline phosphatase prostate cancer antigen, and M phase phosphoprotein 1 bladder cancer antigen.

The optimum reaction conditions may vary according to varying protein characteristics including isoelectric point, grand average of hydropathy, the instability index (an estimate of the stability of protein in a test tube), the elative volume occupied by aliphatic side chains (alanine, valine, isoleucine, and leucine), which is regarded as a positive factor for the increase of thermostability of globular proteins, the number of anionic residues, and the number of cationic residues. Such characteristics are known for a variety of proteins.

The stability of proteins and maintenance of their native conformations are subject to a combination of hydrophobic interactions within their interior domains and the hydrogen bonding and charge interactions on the exterior surface of their structure. As these surface interactions are altered by modification with reagents such as aldehyde-bearing heterobifunctional compounds and compounds of Formula I, the native conformation of the protein may be altered. To provide the conjugate (i.e., the reaction product of the compound or salt of Formula I and the aldehyde-bearing protein), a ratio of the compound or salt to the aldehyde-bearing protein can be varied such that the stability of the protein and its native conformation is maintained. In some embodiments, a ratio of the compound or salt to the aldehyde-bearing protein is in a range from 30:1 to 1:3. In some embodiments, a ratio of the compound or salt to the aldehyde-bearing protein is in a range from 20:1 to 1:2. In some embodiments, a ratio of the compound or salt to the aldehyde-bearing protein is in a range from 10:1 to 1:1. The number of equivalents of the compound or salt of Formula I, for example, may be the same or similar to the number of equivalents of the heterobifunctional linking compound used in some embodiments. In some embodiments in the conjugate, a ratio of the conjugated segment of Formula II to the aldehyde-bearing protein is in a range from 30:1 to 1:6. In some embodiments, a ratio of the conjugated segment of Formula II to the aldehyde-bearing protein is in a range from 20:1 to 1:5. In some embodiments, a ratio of the conjugated segment of Formula II to the aldehyde-bearing protein is in a range from 10:1 to 1:1.

Pharmaceutical Compositions and Methods

A conjugate made from a compound of Formula I or I-A and an aldehyde-bearing antigen (in some embodiments, a conjugate of Formula II) may be administered in a pharmaceutical composition disclosed herein in any suitable manner (e.g., non-parenterally or parenterally). As used herein, non-parenterally refers to administration through the digestive tract, including by oral ingestion. Parenterally refers to administration other than through the digestive tract which would include nasal (e.g., transmucosally by inhalation), topical, ophthalmic, and buccal administration, but in practice usually refers to injection (e.g., intravenous, intramuscular, subcutaneous, intratumoral, or transdermal) using, for example, conventional needle injection, injection using a microneedle array, or any other known method of injection.

A conjugate made from a compound of Formula I or I-A and an aldehyde-bearing antigen (in some embodiments, a conjugate of Formula II) may be provided in any pharmaceutical composition suitable for administration to a subject and may be present in the pharmaceutical composition in any suitable form (e.g., a solution, a suspension, an emulsion, or any form of mixture). The pharmaceutical composition may be formulated with any pharmaceutically acceptable excipient, carrier, or vehicle. The pharmaceutical composition may further include one or more additives including skin penetration enhancers, colorants, fragrances, flavorings, moisturizers, thickeners, suspending agents, surfactants, and dispersing agents.

In addition to antigens specifically described above and below, the pharmaceutical compositions and methods of the present disclosure can include other additional active agents, e.g., in admixture or administered separately. Such additional agents can include a chemotherapeutic agent, a cytotoxoid agent, an antibody, an antiviral agent, a cytokine, a tumor necrosis factor receptor (TNFR) agonist, or an additional immune response modifier. TNFR agonists that may be delivered in conjunction with a conjugate of the present invention (in some embodiments, the conjugate of Formula II) include CD40 receptor agonists, such as disclosed in application U.S. Pat. Appl. Pub. No. 2004/0141950 (Noelle et al.). Other active ingredients for use in combination with an IRM preparation of the present invention include those disclosed in, e.g., U.S. Pat. Appl. Pub. No. 2003/0139364 (Krieg et al.).

Conjugates made from a compound of Formula I or I-A and an aldehyde-bearing antigen (in some embodiments, conjugates of Formula II) have been shown to induce the production of INF-α and TNF-α in human cells as described in the Examples below. The ability to induce INF-α and TNF-α production indicates that the compounds and conjugates of the invention can modulate the immune response in a number of different ways, rendering it useful in the treatment of a variety of disorders. Other cytokines whose production may be induced by the administration of the compounds and conjugates disclosed herein generally include Type I interferons (e.g., INF-α), IL-1, IL-6, IL-8, IL-10, IL-12, MIP-1, MCP-1, and a variety of other cytokines. Among other effects, these and other cytokines inhibit virus production and tumor cell growth, making the compound of Formula I and conjugates made therefrom useful in the treatment of viral diseases and neoplastic diseases. For example, tumor necrosis factor, interferons, or interleukins have been shown to stimulate a rapid release of certain monocyte/macrophage-derived cytokines and are also capable of stimulating B cells to secrete antibodies which play an important role in antiviral and antitumor activities.

In addition to the ability to induce the production of cytokines, the conjugate described herein may affect other aspects of the innate immune response. For example, natural killer cell activity may be stimulated, an effect that may be due to cytokine induction. IRM activity of the conjugate of the present invention also may include activating macrophages, which in turn stimulate secretion of nitric oxide and the production of additional cytokines. IRM activity of the conjugate of the present invention also may include inducing cytokine production by T cells, activating T cells specific to an antigen, and/or activating dendritic cells. Further, IRM activity of the conjugate may include proliferation and differentiation of B-lymphocytes. IRM activity of the conjugate also may affect the acquired immune response. For example, IRM activity can include inducing the production of the T helper type 1 ($T_H1$) cytokine IFN-γ and/or inhibiting the production of the T helper type 2 ($T_H2$) cytokines IL-4, IL-5 and/or IL-13.

In the Examples that follow, a conjugate prepared from a compound of Formula I and hemagglutinin 1 (HA) demonstrates a potent vaccine adjuvant effect with a strong $T_H1$ biased immune response indicated by the increased ratio of HA specific IgG2a to HA specific IgG1 antibody. Such responses are typically accompanied by HA stimulation of T cell interferon gamma production and the generation of cell mediated, cytotoxic T cell immunity towards HA expressing cells, as well as other vaccine antigens. Such antigens may be those associated with and intended for treatment of viral and bacterial infectious diseases as well as various cancers.

Accordingly, the invention provides a method of inducing cytokine biosynthesis in an animal comprising administering an effective amount of the conjugate made from a compound of Formula I or I-A and an aldehyde-bearing antigen (in some embodiments, conjugates of Formula II) (e.g., in a pharmaceutical composition) to the animal.

In some embodiments of the conjugate made from a compound of Formula I or I-A and an aldehyde-bearing antigen (in some embodiments, conjugates of Formula II), the antigen is a vaccine, and methods according to the invention include a method of vaccinating an animal comprising administering to the animal a conjugate prepared from a compound of Formula I and an antigen (in some embodiments, a conjugate of Formula II). Vaccines include any material administered to raise either humoral and/or cell mediated immune response, such as live or attenuated viral and bacterial immunogens and inactivated viral, tumor-derived, protozoal, organism-derived, fungal, and bacterial immunogens, toxoids, toxins, polysaccharides, proteins, glycoproteins, peptides, cellular vaccines (e.g., using dendritic cells), DNA vaccines, recombinant proteins, glycoproteins, and peptides. Exemplary vaccines include vaccines for cancer, BCG, cholera, plague, typhoid, hepatitis A, B, and C, influenza A and B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, severe acute respiratory syndrome (SARS), anthrax, and yellow fever. See also, e.g., vaccines disclosed in International Publication No. WO 02/24225 (Thomsen et al.).

The methods of the present invention may be performed on any suitable subject. Suitable subjects include animals such as humans, non-human primates, rodents, dogs, cats, horses, pigs, sheep, goats, or cows.

The animal to which the conjugate is administered for induction of cytokine biosynthesis or for vaccination may have a disease (e.g., a viral or neoplastic disease), and administration of the compound may provide therapeutic treatment. Also, the conjugate may be administered to the animal before the animal acquires the disease so that administration of the conjugate may provide a prophylactic treatment. For example, a conjugate may be made from a compound of Formula I or I-A and an HIV antigen and may provide therapeutic and/or prophylactic treatment for HIV. In another example, a conjugate may be made from a compound of Formula I or I-A and a tumor-associated antigen and may provide therapeutic and/or prophylactic treatment against a tumor associated with the antigen.

Exemplary conditions that may be treated by administering an IRM conjugate include:

(a) viral diseases such as diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases such as chlamydia, fungal diseases (e.g., candidiasis, aspergillosis, histoplasmosis, or cryptococcal meningitis), or parasitic diseases (e.g., malaria, pneumocystis carnii pneumonia, leishmaniasis, cryptosporidiosis, toxoplasmosis, and trypanosome infection);

(d) neoplastic diseases such as intraepithelial neoplasias, cervical dysplasia, actinic keratosis, basal cell carcinoma, squamous cell carcinoma, renal cell carcinoma, Kaposi's sarcoma, melanoma, leukemias (e.g., myelogenous leukemia, chronic lymphocytic leukemia, multiple myeloma, non-Hodgkin's lymphoma, cutaneous T-cell lymphoma, B-cell lymphoma, and hairy cell leukemia), breast cancer, lung cancer, prostate cancer, colon cancer, and other cancers;

(e) $T_H2$-mediated, atopic diseases such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, and alopecia greata; and (g) diseases associated with wound repair such as inhibition of keloid formation and other types of scarring (e.g., enhancing wound healing, including chronic wounds).

IRM conjugates also may be useful to individuals having compromised immune function. For example, certain conjugates may be useful for treating the opportunistic infections and tumors that occur after suppression of cell mediated immunity in, for example, transplant patients, cancer patients, and HIV patients.

It will be understood that in the treatment of the diseases mentioned above, for example, the conjugate disclosed herein can be used in combination with other therapies such as the active agents mentioned above and other procedures (e.g., chemoablation, laser ablation, cryotherapy, and surgical excision).

An amount of a conjugate effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-1O and IL-12 that is increased over a background level of such cytokines. The precise amount will vary according to factors known in the art but is expected to be a dose of about 100 nanograms per kilograms (ng/kg) to about 50 milligrams per kilogram (mg/kg), in some embodiments about 10 micrograms per kilogram (μg/kg) to about 5 mg/kg, about 100 μg/kg to about 1 mg/kg, or about 0.01 $mg/m^2$ to about 10 $mg/m^2$. Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2$=(wt $kg^{0.425}$×height $cm^{0.725}$)×0.007184. An amount effective to treat or inhibit a viral infection, for example, is an amount that will cause a reduction in one or more of the manifestations of viral infection, such as viral lesions, viral load, rate of virus production, and mortality as compared to untreated control animals and may include any of the aforementioned doses. An amount of a compound or pharmaceutical composition effective to treat a neoplastic condition is an amount that will cause a reduction in tumor size or in the number of tumor foci and may include any of the aforementioned doses.

The composition of a formulation suitable for practicing the invention, the precise amount of a conjugate effective for methods according to the present invention, and the dosing regimen, for example, will vary according to factors known in the art including the nature of the carrier, the state of the subject's immune system (e.g., suppressed, compromised, stimulated), the method of administering the conjugate, and the species to which the formulation is being administered. Accordingly, it is not practical to set forth generally the composition of a formulation that includes a conjugate made from a compound of Formula I or I-A, an amount of the conjugate that constitutes an effective amount, or a dosing regimen that is effective for all possible applications. Those of ordinary skill in the art, however, can readily determine appropriate formulations, amounts of the conjugate, and dosing regimen with due consideration of such factors.

In some embodiments, the methods of the present invention include administering a conjugate to a subject in a formulation, for example, having a concentration of the compound from about 0.0001% to about 20% (unless otherwise indicated, all percentages provided herein are weight/weight with respect to the total formulation), although in some embodiments the conjugate may be administered using a formulation that provides the compound in a concentration outside of this range. In some embodiments, the method includes administering to a subject a formulation that includes from about 0.01% to about 1% of the conjugate, for example, a formulation that includes about 0.1% to about 0.5% compound of the conjugate.

In some embodiments of the methods disclosed herein, the conjugate may be administered, for example, from a single dose to multiple doses per week, although in some embodiments the methods of the present invention may be performed by administering the conjugate at a frequency outside this range. In some embodiments, the conjugate may be administered from about once per month to about five times per week. In some embodiments, the conjugate is administered once per week.

The conjugate may also be used as a booster following initial immunization with a DNA or RNA vaccine encoding, whole or in part, the same antigen.

Some Embodiments of the Invention:

In a first embodiment, the present invention provides a compound of Formula (I):

I

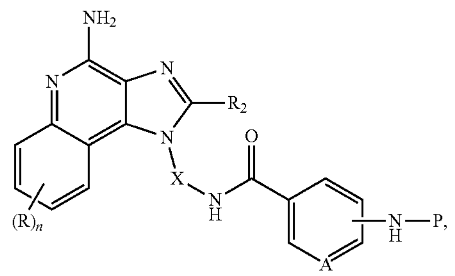

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

P is an amino group, a protected amino group, or $NH_3^+Y^-$, wherein $Y^-$ is a counter anion;

A is CH or N;

R is halogen, hydroxyl, alkyl, haloalkyl, or alkoxy; and n is an integer from 0 to 4;

or a pharmaceutically acceptable salt thereof.

In a second embodiment, the present invention provides the compound or salt according to the first embodiment, wherein P is an amino group (i.e., —$NH_2$).

In a third embodiment, the present invention provides a compound of Formula (I-A):

I-A

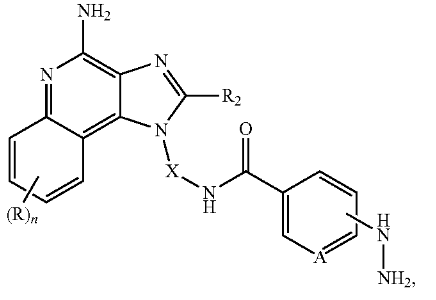

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

A is CH or N;

R is halogen, hydroxyl, alkyl, haloalkyl, or alkoxy; and n is an integer from 0 to 4;

or a pharmaceutically acceptable salt thereof.

In a fourth embodiment, the present invention provides the compound or salt of any one of the first to third embodiments, wherein n is 0.

In a fifth embodiment, the present invention provides the compound or salt of any one of the first to fourth embodiments, wherein $R_2$ is methyl, ethyl, propyl, butyl, ethoxymethyl, methoxymethyl, ethylaminomethyl, or 2-methoxyethyl. In some of these embodiments, $R_2$ is methyl, ethyl, propyl, butyl, ethoxymethyl, methoxymethyl, or 2-methoxyethyl.

In a sixth embodiment, the present invention provides the compound or salt of any one of the first to fifth embodiments, wherein X is —O—$C_{3-8}$alkylene.

In a seventh embodiment, the present invention provides the compound or salt of any one of the first to fifth embodiments, wherein X is —O—$C_{3-5}$alkylene.

In an eighth embodiment, the present invention provides the compound or salt of the second or third embodiment, which is of formula:

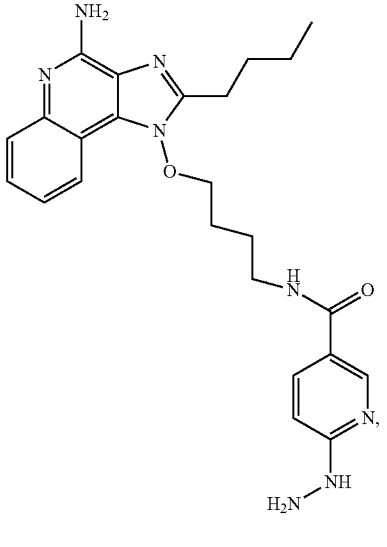 [SMILES: CCCCc1nc2c(N)nc3ccccc3c2n1OCCCCNC(=O)c1ccc(NN)nc1]

or a pharmaceutically acceptable salt thereof.

In a ninth embodiment, the present invention provides the compound or salt of the first embodiment, which is of formula:

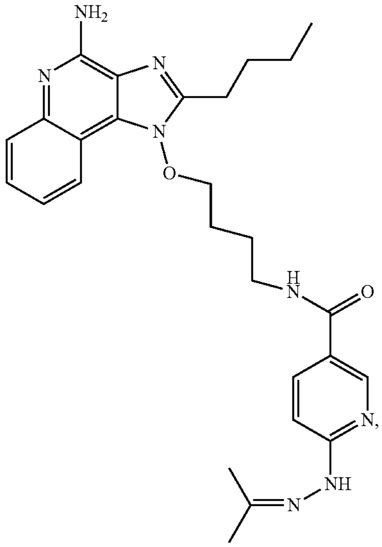 [SMILES: CCCCc1nc2c(N)nc3ccccc3c2n1OCCCCNC(=O)c1ccc(NN=C(C)C)nc1]

or a pharmaceutically acceptable salt thereof.

In a tenth embodiment, the present invention provides the compound or salt of any one of the first to fifth embodiments, wherein X is —$C_{3-8}$alkylene.

In an eleventh embodiment, the present invention provides the compound or salt of any one of the first to fifth embodiments, wherein X is —$C_{3-5}$alkylene.

In a twelfth embodiment, the present invention provides a conjugate comprising a reaction product of the compound or salt of any one of the first to eleventh embodiments and an aldehyde-bearing antigen.

In an thirteenth embodiment, the present invention provides a conjugate comprising a hydrazonobenzamide 1H-imidazo[4,5-c]quinolin-4-amine or hydrazononicotinamide 1H-imidazo[4,5-c]quinolin-4-amine formed by reaction of the compound or salt of any one of the first to eleventh embodiments and an aldehyde-bearing antigen.

In a fourteenth embodiment, the present invention provides the conjugate of the twelfth or thirteenth embodiment, wherein the aldehyde-bearing antigen is an aldehyde-bearing protein.

In a fifteenth embodiment, the present invention provides the conjugate of the fourteenth embodiment, wherein to provide the reaction product, a ratio of the compound or salt to the aldehyde-bearing protein is in a range from 30:1 to 1:3.

In a sixteenth embodiment, the present invention provides the conjugate of the twelfth or thirteenth embodiment, wherein the aldehyde-bearing antigen is an aldehyde-bearing lipid.

In a seventeenth embodiment, the present invention provides a conjugate of an antigen, the conjugate having at least one segment represented by formula:

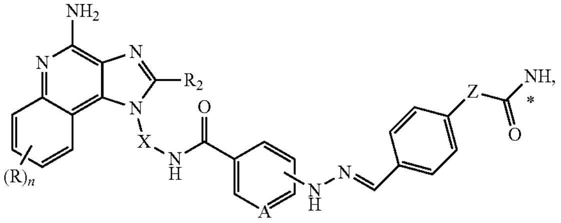

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

A is CH or N;

R is halogen, hydroxyl, alkyl, haloalkyl, or alkoxy;

n is an integer from 0 to 4;

Z is a bond or —C(O)—NH—$(CH_2CH_2O)_p$—$CH_2CH_2$—, wherein p is in a range from 1 to 50; and the nitrogen atom indicated by N* is covalently bonded to the antigen;

or a pharmaceutically acceptable salt thereof.

In an eighteenth embodiment, the present invention provides the conjugate of the seventeenth embodiment, wherein n is 0.

In a nineteenth embodiment, the present invention provides the conjugate of the seventeenth or eighteenth embodiment, wherein $R_2$ is methyl, ethyl, propyl, butyl, ethoxymethyl, methoxymethyl, ethylaminomethyl, or 2-methoxyethyl. In some of these embodiments, $R_2$ is methyl, ethyl, propyl, butyl, ethoxymethyl, methoxymethyl, or 2-methoxyethyl.

In a twentieth embodiment, the present invention provides the conjugate of any one of the seventeenth to nineteenth embodiments, wherein X is —O—$C_{3-8}$alkylene.

In a twenty-first embodiment, the present invention provides the conjugate of the twentieth embodiment, wherein X is —O—$C_{3-5}$alkylene.

In a twenty-second embodiment, the present invention provides the compound or salt of any one of the seventeenth to nineteenth embodiments, wherein X is $C_{3-8}$alkylene.

In a twenty-third embodiment, the present invention provides the compound or salt of the twenty-second embodiment, wherein X is $C_{3-5}$alkylene.

In a twenty-fourth embodiment, the present invention provides the conjugate of any one of the seventeenth to twenty-third embodiments, wherein the antigen is a protein.

In a twenty-fifth embodiment, the present invention provides the conjugate of any one of the seventeenth to twenty-fourth embodiments, wherein Z is a bond.

In a twenty-sixth embodiment, the present invention provides the conjugate of any one of the seventeenth to twenty-fourth embodiments, wherein Z is —C(O)—NH—$(CH_2CH_2O)_p$—$CH_2CH_2$—, wherein p is in a range from 1 to 50.

In a twenty-seventh embodiment, the present invention provides a pharmaceutical composition comprising a pharmaceutically acceptable carrier and an effective amount of the conjugate of any one of the twelfth to twenty-sixth embodiments.

In a twenty-eighth embodiment, the present invention provides a method of vaccinating an animal, the method comprising administering an effective amount of the conjugate of any one of the twelfth to twenty-sixth embodiments or the pharmaceutical composition of the twenty-seventh embodiment to the animal.

In a twenty-ninth embodiment, the present invention provides a method of stimulating an antigen-specific response in an animal, the method comprising administering an effective amount of the conjugate of any one of the twelfth to twenty-sixth embodiments or the pharmaceutical composition of the twenty-seventh embodiment to the animal.

In a thirtieth embodiment, the present invention provides a method of inducing cytokine biosynthesis in an animal, the method comprising administering an effective amount of the conjugate of any one of the twelfth to twenty-sixth embodiments or the pharmaceutical composition of the twenty-seventh embodiment to the animal.

In a thirty-first embodiment, the present invention provides a conjugate or pharmaceutical composition for use in vaccinating an animal by administering an effective amount of the conjugate of any one of the twelfth to twenty-sixth embodiments or the pharmaceutical composition of the twenty-seventh embodiment to the animal.

In a thirty-second embodiment, the present invention provides a conjugate or pharmaceutical composition for use in stimulating an antigen-specific response in an animal by administering an effective amount of the conjugate of any one of the twelfth to twenty-sixth embodiments or the pharmaceutical composition of the twenty-seventh embodiment to the animal.

In a thirty-third embodiment, the present invention provides a conjugate or pharmaceutical composition for use in inducing cytokine biosynthesis in an animal by administering an effective amount of the conjugate of any one of the twelfth to twenty-sixth embodiments or the pharmaceutical composition of the twenty-seventh embodiment to the animal.

In a thirty-fourth embodiment, the present invention provides a composition comprising the compound or salt of any one of the first to eleventh embodiments, an aldehyde-bearing antigen, and a pharmaceutically acceptable carrier.

In a thirty-fifth embodiment, the present invention provides a method of making a conjugate, the method comprising:

combining a compound or salt of the first embodiment or any one of the fourth to seventh or tenth embodiments except where they are dependent from the second or third embodiment, wherein P is a protected amino group; an aldehyde-bearing antigen, and a carrier under conditions where the protected amino group is deprotected and the conjugate is formed.

Embodiments of this invention are further illustrated by the following non-limiting examples, but the particular materials and amounts thereof recited in these examples, as well as other conditions and details, should not be construed to unduly limit this invention.

EXAMPLES

Example 1

N-(4-{[4-Amino-2-butyl-1H-imidazo[4,5-c]quinolin-1-yl]oxy}butyl)-6-(N'-isopropylidenehydrazino) nicotinamide (Compound 1) and N-(4-{[4-Amino-2-butyl-1H-imidazo[4,5-c]quinolin-1-yl]oxy} butyl)-6-hydazinonicotinamide (Compound 2)

(Compound 1)

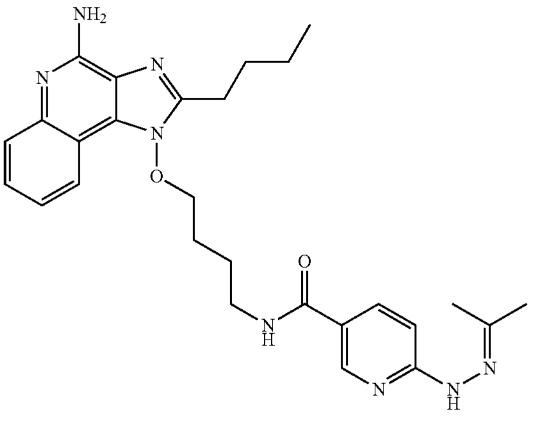

-continued (Compound 2)

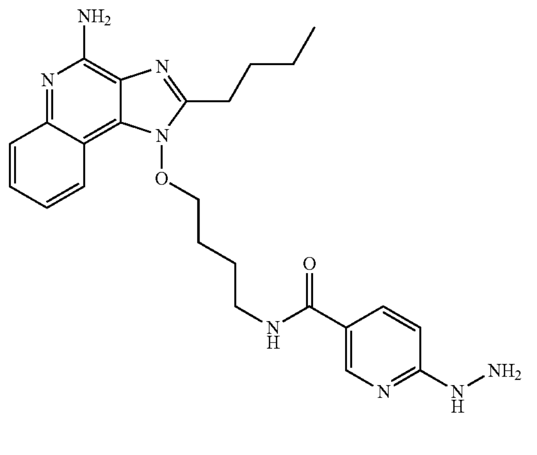

Part A

A solution of valeric anhydride (6.03 g) and pyridine hydrochloride (0.198 g) in pyridine (8.28 g) was added to a solution of 3-amino-4-chloroquinoline (2.94 g) in pyridine (5.0 g) and the reaction was stirred at room temperature for 16 hours followed by heating at 60° C. for 3 hours. The reaction was concentrated under reduced pressure and sodium carbonate (15 mL of a 10% aqueous solution) was added. The reaction was stirred for 30 minutes and then filtered. The resulting solid was washed with water (60 mL) and dried under vacuum for 4 hours to provide 4.59 g of crude N-(4-chloroquinolin-3-yl)valeramide as brown flakes. The crude product was recrystallized from heptane (10 mL) and the recovered product was further purified by soxhlet extraction using refluxing heptane for 16 hours. The collection flask from the soxhlet extraction apparatus was cooled in a freezer for 2 hours. The resulting solid was collected by filtration and dried under vacuum to yield 2.00 g of N-(4-chloroquinolin-3-yl)valeramide as a white solid.

Part B

A solution of 4-amino-1-butanol (7.68 g) and pyridine (7.00 g) in dichloromethane (100 mL) was chilled in an ice bath and a solution of benzylchloroformate (14.37 g) in dichloromethane (100 mL) was slowly added with stirring over a period of thirty minutes. The ice bath was removed and the reaction was stirred for an additional 16 hours. Hydrochloric acid (1.2 M, 200 mL) was added and phases were separated. The organic phase was dried ($MgSO_4$), filtered and concentrated under reduced pressure. The resulting residue was recrystallized from toluene and dried under vacuum to provide 5.15 g of benzyl (4-hydroxybutyl)carbamate.

A solution of N-hydroxyphthalimide (3.36 g), benzyl (4-hydroxybutyl)carbamate (4.18 g) and triphenylphosphine (7.41 g) in dichloromethane (100 mL) was chilled in an ice bath and approximately two-thirds of a solution of diisopropylazodicarboxylate (DIAD, 5.68 g) in dichloromethane (50 mL) was slowly added with stirring. The internal temperature of the reaction was monitored and the addition of the DIAD solution was stopped when an exotherm could no longer be detected. The ice bath was removed and the reaction was allowed to warm to room temperature. The reaction was concentrated under reduced pressure and the resulting residue was dissolved in ethanol (200 proof, 100 mL). Hydrazine (1.98 g, 35% in water) was added and the reaction was stirred for 6 hours. The reaction was cooled in the freezer and the resulting solid was removed by filtration. The solid was washed with ethanol (50 mL). The combined filtrate was concentrated under reduced pressure and diethyl ether (100 mL) was added. Insoluble impurities were removed by filtration and 2.0 M HCl in ether (10 mL) was added to the solution. A precipitate formed immediately. The crude product was added to toluene (100 mL) and heated at reflux temperature for one hour. After cooling to room temperature, the solid product was recovered by filtration, washed with toluene, and dried under vacuum to yield 3.76 g of benzyl (4-aminooxybutyl)carbamate.

Part C

N-(4-Chloroquinolin-3-yl)valeramide (1.97 g), benzyl (4-aminooxybutyl)carbamate (2.99 g), triethylamine (0.89 g) and 2-propanol (40.69 g) were combined and heated at 80° C. for 3.5 hours. The reaction was cooled to room temperature, filtered, and the filtrate concentrated under reduced pressure. Dichloromethane (20 mL) was added to the resulting solid and the mixture was stirred for twenty minutes. Undissolved solid was removed by filtration and the filtrate was washed with two 10 mL portions of water that had been made slightly acidic by the addition of 20 drops of hydrochloric acid (1.2 M). The organic fraction was dried and concentrated under reduced pressure. The crude solid was recrystallized from tetrahydrofuran to provide 2.56 g of benzyl 4-{[2-butyl-1H-imidazo[4,5-c]quinolin-1-yl]oxy}butylcarbamate.

Part D

Benzyl 4-{[2-butyl-1H-imidazo[4,5-c]quinolin-1-yl]oxy}butylcarbamate hydrochloride (10.05 g) was dissolved in dichloromethane (80 mL) and extracted with a solution of sodium carbonate (2.02 g) in 30 mL $H_2O$. The organic layer was cooled in an ice bath and a solution of m-chloroperbenzoic acid (5.93 g, 1.24 eq) dissolved in dichloromethane (30 mL) was slowly added. After 6 hr, ammonium hydroxide (10 mL of a 28-30% aqueous solution) was added to the reaction. A solution of benzenesulfonyl chloride (6.96 g) dissolved in 10 mL dichloromethane was slowly added with vigorous stirring. The cooling bath was removed and the reaction was stirred for an additional 12 hours. The reaction was diluted with water (100 mL) and the organic and aqueous fractions were separated. The aqueous fraction was extracted with dichloromethane (30 mL). The combined organic fractions were washed with two 90 mL portions of 5% sodium carbonate.

The dichloromethane solution was transferred to a distillation apparatus and 1-pentanol (50 mL) was added. This was warmed to 40° C. and the dichoromethane was removed under reduced pressure. Concentrated hydrochloric acid (50 mL) was then added and the reaction was stirred and heated to 80° C. After 11 hours, the solution was cooled to room temperature and diluted with water (100 mL). The aqueous fraction was separated from the 1-pentanol and the 1-pentanol was extracted with water (25 mL). The aqueous fractions were combined. 1-Pentanol (50 mL) was added to the combined aqueous fraction and this was cooled in an ice-bath. With vigorous stirring, solid sodium carbonate was added to bring the pH to 9-10. The mixture was transferred to a separatory funnel and the fractions were separated. The aqueous fraction was extracted with two 25 mL portions of 1-pentanol. The combined 1-pentanol fractions were dried over sodium sulfate and filtered to provide 1-(4-aminobutoxy)-2-butyl-1H-imidazo[4,5-c]quinolin-4-amine dissolved in 1-pentanol.

The maleate salt of 1-(4-aminobutoxy)-2-butyl-1H-imidazo[4,5-c]quinolin-4-amine was prepared by dissolving maleic acid (4.83 g) in 1-pentanol (50 mL) and adding it with stirring to the solution of 1-(4-aminobutoxy)-2-butyl-1H-imidazo[4,5-c]quinolin-4-amine in 1-pentanol. The resulting precipitate was collected by filtration and dried to yield 7.69 g of 1-(4-aminobutoxy)-2-butyl-1H-imidazo[4,5-c]quinolin- 4-amine bis maleate salt. $^1$H-NMR (DMSO-d6): δ 0.96 (t, 3H), 1.44 (m, 2H), 1.7-1.95 (m, 4H), 2.02 (m, 2H), 2.8-3.1 (m, 4H), δ 4.43 (t, 2H), 6.07 (s, 4H), 7.57 (t, 1H), 7.73 (t, 1H), 7.80 (d, 1H), 8.16 (d, 1H). Broad peaks for the ammonium protons are seen at approximately δ 7.8 and δ 8.7.

Part E

The 1-(4-aminobutoxy)-2-butyl-1H-imidazo[4,5-c]quinolin-4-amine bis maleate salt (0.2 g) was suspended in 1-butanol (5 mL) and washed sequentially with 2×5 mL portions of a 5% sodium carbonate solution followed by 5 mL of a saturated sodium chloride solution. Succinimidyl 4-hydrazinonicotinate acetone hydrazone (SANH, 0.0216 g); available from Thermo Scientific, Rockford, Ill.; was added and the solution was stirred at ambient temperature for 17.5 hours. Analysis of the reaction by thin layer chromatography (silica gel, eluent of 1:1 methyl-tert-butylether:ethanol) showed only the presence of 1-(4-aminobutoxy)-2-butyl-1H-imidazo[4,5-c]quinolin-4-amine ($R_f$<0.05) and the desired product N-(4-{[4-amino-2-butyl-1H-imidazo[4,5-c]quinolin-1-yl]oxy}butyl)-6-(N'-isopropylidenehydrazino)nicotinamide ($R_f$ 0.30). The reaction was concentrated under reduced pressure and 5 mL of dichloromethane was added to the residue. Small amounts of insoluble material were removed by filtration and the sample was purified by column chromatography (silica gel, eluent of 1:1 methyl-tert-butylether:ethanol). The fractions containing product were combined and the solvent removed under reduced pressure to provide N-(4-{[4-amino-2-butyl-1H-imidazo[4,5-c]quinolin-1-yl]oxy}butyl)-6-(N'-isopropylidenehydrazino)nicotinamide as a light yellow solid (compound 1).

$^1$H NMR (chloroform-d) δ: 8.59 (d, J=2.2 Hz, 1H), 7.81-8.15 (m, 3H), 7.75 (d, J=8.1 Hz, 1H), 7.48 (t, J=7.6 Hz, 1H), 7.28 (t, J=7.5 Hz, 1H), 7.20 (d, J=8.7 Hz, 1H), 6.57 (t, J=5.6 Hz, 1H), 5.61 (br. s., 2H), 4.24 (t, J=6.1 Hz, 2H), 3.55 (q, J=6.3 Hz, 2H), 2.88 (t, J=7.6 Hz, 2H), 1.93-2.12 (m, 5H), 1.74-1.93 (m, 7H), 1.37-1.54 (m, 2H), 0.96 (t, J=7.2 Hz, 3H).

Part F

The N-(4-{[4-amino-2-butyl-1H-imidazo[4,5-c]quinolin-1-yl]oxy}butyl)-6-(N'-isopropylidenehydrazino)nicotinamide from Part E was suspended in 1 mL of hydrochloric acid (0.6 M) and heated at 60° C. for 90 minutes. The resulting homogeneous solution was cooled to ambient temperature and the reaction was concentrated under reduced pressure. The resulting residue was dissolved in water and lyophilized to provide 43.6 mg of N-(4-{[4-amino-2-butyl-1H-imidazo[4,5-c]quinolin-1-yl]oxy}butyl)-6-hydazinonicotinamide hydrochloride salt as a yellow solid (Compound 2). MS (ESI) m/z 463.25661 (463.25645 calcd for $C_{24}H_{31}N_8O_2$, M+H$^+$).

Example 2

Recombinant hemagglutinin 1 (HA) from H1N1 PR8 was cloned, expressed in *E. coli*, and purified using standard procedures. The HA, molecular weight 32083.11 daltons, bearing 6 histidines at the C terminus, was placed in a pH 7.5, 0.1 M phosphate buffer, containing 0.15 M NaCl. Based on the molecular weight of the HA and the mass of protein, the molarity of the HA solution was established. Succinimidyl 4-formylbenzoate (SFB) (Thermo Scientific, Rockford, Ill.) dissolved in dimethyl sulfoxide (DMSO) was added to HA at a 10 fold molar excess. The solution was then incubated for 2 hours at room temperature. A control sample of HA was incubated with an equivalent volume of DMSO in a similar manner. SFB-modified HA (represented as HA-SFB) was separated from free SFB by use of a ZEBA spin column (Thermo Scientific, Rockford, Ill.) pre-equilibrated with pH 6.0, 0.1M phosphate buffer containing 0.15 M NaCl. This step changed the HA-SFB solution to pH 6.0 in preparation for the conjugation reaction.

In order to determine the efficiency of covalent conjugation, N-(4-{[4-amino-2-butyl-1H-imidazo[4,5-c]quinolin-1-yl]oxy}butyl)-6-(N'-isopropylidenehydrazino)nicotinamide (Compound 1 of Example 1) was dissolved in DMSO and added to the buffered HA-SFB solution in amounts of 30, 10, 3 and 1 fold molar excess. The acidic condition of the reaction medium resulted in deprotection of the acetimine protecting group of compound 1 to form Compound 2 in situ. Each of the four test samples were incubated for 2 hours at room temperature. The control HA-SFB sample was incubated with an equivalent volume of DMSO in a similar manner HA-SFB covalently conjugated to Compound 2 of Example 1 (represented as HA-SFB-Compound 2) was separated from unconjugated components by use of a ZEBA spin column pre-equilibrated with Dulbecco's phosphate buffered saline (PBS) (Sigma-Aldrich, St. Louis, Mo.).

The efficiency of incorporation of Compound 2 into HA through covalent conjugation was determined by using a UV spectrophotometric assay and the results are recorded in Table 1. The bis-aromatic hydrazone bond that is formed by covalent conjugation of HA-SFB with Compound 2 provides a distinctive chromophore. The chromophore has a maximal absorbance a 354 nm and a molar extinction coefficient equal to 29,000. The number of moles of compound 1 incorporated into the HA protein was calculated by dividing the measured absorbance of the conjugated HA-SFP-Compound 2 at 354 nm by the molar extinction coefficient of 29,000. The results are shown in Table 1, below.

TABLE 1

| Molar Ratio of Compound 1 reacted with HA-SFB Protein | Moles of Compound 2 Covalently Conjugated to a Mole of HA-SFB Protein |
|---|---|
| 30:1 | 1.4 |
| 10:1 | 6.1 |
| 3:1 | 3.4 |
| 1:1 | 0.2 |

Example 3

A covalently conjugated product (HA-SFB-Compound 2) was prepared by adding a 10 fold molar excess of Compound 1 to HA-SFB according to the procedure described in Example 2. The in vitro induction of interferon-α (IFN) and tumor necrosis factor (TNF) production in human peripheral mononuclear cells (PBMC) by the conjugated product was determined. The PBMCs were prepared from human volunteers and placed in culture in 96 well microtiter plates. HA, HA-SFB, and HA-SFB-Compound 2 conjugate, respectively, were added to the wells at a final concentration of 1 μM protein. The cells were then incubated overnight at 37° C. The medium was removed and IFN concentration (pg/mL) and TNF concentration (ng/mL) were measured by ELISA assay. The results of the assay are reported in Table 2, below.

TABLE 2

| Agent added to PBMC | TNF (ng/mL) | IFN (pg/mL) |
|---|---|---|
| None | Not Detected | Not Detected |
| HA | 3.71 | 17.00 |
| HA-SFB | 2.30 | Not Detected |
| HA-SFB-Compound 2 | 11.28 | 161.60 |

Example 4

The vaccine adjuvant activity of Compound 2 covalently conjugated to recombinant hemagglutinin 1 (HA) (HA-SFB-Compound 2) was evaluated in Balb/C male mice (Charles River Laboratories, International, Wilmington, Mass.). Groups of 5 mice each were immunized subcutaneously with 10 microgram of HA antigen in PBS (control), 10 microgram of HA antigen conjugated to SFB (control), or HA antigen modified with SFB and then conjugated to Compound 2 of Example 1. The conjugated product was prepared by adding a 10 fold molar excess of Compound 1 to HA-SFB according to the procedure described in Example 2. The mice were boosted with the same combinations 2 weeks and 4 weeks following the initial immunization. Three weeks and again at 12 weeks following the final boost, the mice were bled and the HA-specific antibody titers were determined. This determination was performed by serial dilution of the serum samples by standard serum ELISA in HA-coated microtiter plates. The antibody data is presented as the serum dilution achieving the end point (2× baseline) and is the geometric mean for the 5 mice per each group. As an index of TH1 bias of the immune response, HA-specific IgG1 and IgG2a subtypes were measured, in addition to HA-specific total IgG. The experimental results are reported in Table 3.

Compound 2 covalently conjugated to HA through hydrazone linking groups demonstrates a potent vaccine adjuvant effect with a strong TH1 biased immune response indicated by the increased ratio of HA specific IgG2a to HA specific IgG1 antibody.

TABLE 3

| In Vivo Immunization | HA Specific IgG1 | | HA Specific IgG2a | | HA Specific Total IgG | |
|---|---|---|---|---|---|---|
| Agent | 3 weeks | 12 weeks | 3 weeks | 12 weeks | 3 weeks | 12 weeks |
| HA | 7.7E+5 | 4.3E+5 | 5.9E+3 | 6.7E+3 | 3.3E+5 | 7.7E+5 |
| HA-SFB | 7.7E+5 | 4.4E+5 | 2.5E+4 | 6.7E+3 | 4.3E+5 | 7.7E+5 |
| HA-SFB-Compound 2 | 4.3E+6 | 4.3E+6 | 1.1E+6 | 8.8E+5 | 1.0E+7 | 1.0E+7 |

Preparation of (Compound 3)

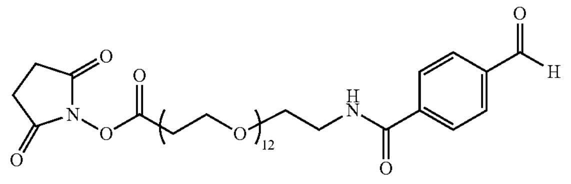

Part A

CA(PEG)12 (formula of $H_2N—CH_2CH_2—(OCH_2CH_2)_{12}—CO_2H$; MW=617.7; available from Thermo Scientific, Rockford, Ill., 115 mg) dissolved in dry dichloromethane (5 mL), N-Succinimidyl-4-formylbenzoate (52 mg dissolved in dry dichloromethane (0.5 mL); available from EMD Chemicals, Gibbstown, N.J.), dry triethylamine (52 μL), and a catalytic amount of DMAP were combined under an atmosphere of nitrogen. The reaction was stirred for 3 hours and then diluted with dichloromethane (25 mL). The organic fraction was washed with 0.1 M sodium phosphate (2×10 mL) followed by brine. The organic fraction was dried over sodium sulfate, filtered, and concentrated under reduced pressure. The aqueous wash fractions were combined and extracted with several portions of dichloromethane. The aqueous fraction was then acidified to pH ~2 with dilute hydrochloric acid and extracted with two additional portions of dichloromethane. The organic extracts were combined, dried over sodium sulfate, filtered, and concentrated under reduced pressure. The resulting material was combined with the material obtained from the first extraction and purified using a small column of silica gel. Elution with 10-25% methanol/chloroform, saturated with water, yielded 58 mg of the amide product as a colorless solid. $^1$H NMR (chloroform-d, 500 MHz) δ 10.08 (s, 1H), 8.00 (d, J=8.2 Hz, 2H), 7.95 (d, J=8.4 Hz, 2H), 7.19 (m, 1H), 3.77 (t, J=6.1 Hz, 2H), 3.70-3.60 (m, 48H), 2.60 (t, J=6.1 Hz, 2H).

Part B

The material from Part A was dissolved in dry N,N-dimethylformamide (0.5 mL) and dry pyridine (0.5 mL). O—(N-Succinimidyl)-1,1,3,3-tetramethyluronium tetrafluoroborate (TSTU; 46 mg; available from Sigma-Aldrich, St. Louis, Mo.) was added and the reaction was stirred under a nitrogen atmosphere for 3 hours. Most of the solvent was removed under reduced pressure. The resulting material was dissolved in chloroform (25 mL) and methanol (5 mL) and placed in a separatory funnel A buffer solution (10 mL of a solution of 0.10 M sodium chloride, 0.05 M sodium phosphate, 1.0 mM EDTA adjusted to pH 7.5 with sodium hydroxide) was added and the mixture was shaken for 2 minutes. The organic fraction was collected and washed sequentially with an additional portion of the buffer solution (10 mL), water (3×10 mL), and brine. The organic fraction was dried over sodium sulfate, filtered, and concentrated under reduced pressure to provide 55 mg of Compound 3 as a colorless syrup. $^1$H NMR (chloroform-d, 500 MHz) δ 10.08 (s, 1H), 7.99 (d, J=8.2 Hz, 2H), 7.95 (d, J=8.1 Hz, 2H), 7.10 (m, 1H), 3.85 (t, J=6.5 Hz, 2H), 3.70-3.60 (m, 48H), 2.90 (t, J=6.9 Hz, 2H) 2.84 (br s, 4H).

Example 5

Example 5 was prepared according to the method of Example 2, with the modification that compound 3 dissolved in dimethyl sulfoxide (DMSO) was added to HA at a 10 fold molar excess to provide a Compound 3-modified HA (represented as HA-Compound 3).

N-(4-{[4-Amino-2-butyl-1H-imidazo[4,5-c]quinolin-1-yl]oxy}butyl)-6-(N'-isopropylidenehydrazino)nicotinamide (Compound 1 of Example 1) was dissolved in DMSO and added to the buffered HA-Compound 3 solution in a 10-fold molar excess. The acidic conditions of the reaction medium resulted in deprotection of the acetimine protecting group of Compound 1 to form Compound 2 in situ. The sample was incubated for 2 hours at room temperature. HA-Compound 3 covalently conjugated to Compound 2 of Example 1 (represented as HA-Compound 3-Compound 2) was separated from unconjugated components by use of a ZEBA spin column pre-equilibrated with Dulbecco's phosphate buffered saline (PBS) (Sigma-Aldrich, St. Louis, Mo.).

Compound 1 was dissolved in DMSO and added to buffered HA-SFB solution in a 10 fold molar excess according to the procedure described in Example 2 to provide HA-SFB covalently conjugated to Compound 2 of Example 1 (represented as HA-SFB-Compound 2).

The effect of using Compound 3 in the covalently conjugated product, as compared to SFB, on final protein solubility and percent recovery is shown in Table 4. The soluble protein measurement was determined as the amount of HA-SFB-Compound 2 or HA-Compound 3-Compound 2 recovered in the supernatant of a 100K×g centrifuged sample. The total protein measurement was determined as the amount of HA-SFB-Compound 2 or HA-Compound 3-Compound 2 in the sample prior to centrifugation. Soluble protein and total protein measurements were made using a Bicinchoninic Acid (BCA) Protein Assay (obtained from Thermo Scientific, Rockford, Ill.).

TABLE 4

| Protein Sample (prepared according to Example 5) | Total Protein (μg/ml) | Soluble Protein (μg/ml) | Percent Recovery |
|---|---|---|---|
| HA-SFB-Compound 2 | 630.2 | 215.8 | 34.2% |
| HA-Compound 3-Compound 2 | 686.9 | 659.3 | 95.9% |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of formula:

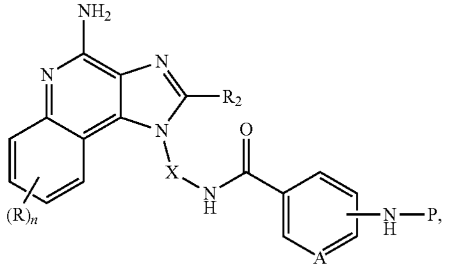

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

P is an amino group, a protected amino group, or $NH_3^+Y^-$, wherein $Y^-$ is a counter anion;

A is CH or N;

R is halogen, hydroxyl, alkyl, haloalkyl, or alkoxy; and n is an integer from 0 to 4;

or a pharmaceutically acceptable salt thereof.

2. The compound or salt of claim 1, wherein P is an amino group.

3. The compound or salt of claim 1, wherein n is 0.

4. The compound or salt of claim 1, wherein $R_2$ is methyl, ethyl, propyl, butyl, ethoxymethyl, methoxymethyl, ethylaminomethyl, or 2-methoxyethyl.

5. The compound or salt of claim 1, wherein X is —O—$C_{3-8}$alkylene.

6. The compound or salt of claim 1, which is of formula:

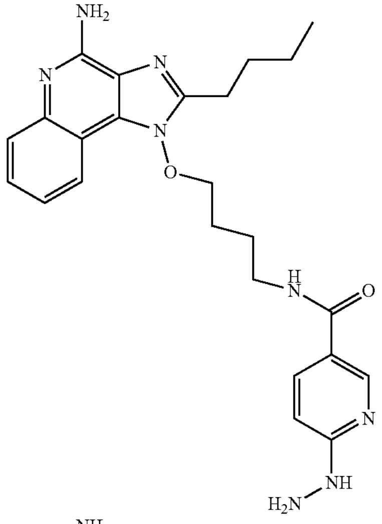

or

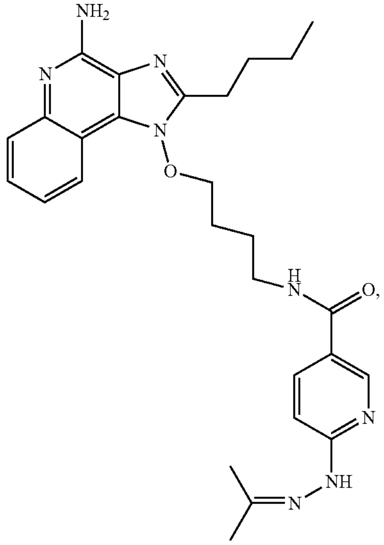

or a pharmaceutically acceptable salt thereof.

7. The compound or salt of claim 1, wherein X is $C_{3-8}$alkylene.

8. A conjugate comprising a reaction product of the compound or salt of claim 1 and an aldehyde-bearing antigen.

9. The conjugate of claim 8, wherein the aldehyde-bearing antigen is an aldehyde-bearing protein.

10. The conjugate of claim 9, wherein to provide the reaction product, a ratio of the compound or salt to the aldehyde-bearing protein is in a range from 30:1 to 1:3.

11. The conjugate of claim 8, wherein the aldehyde-bearing antigen is an aldehyde-bearing lipid.

12. A conjugate of an antigen, the conjugate having at least one segment represented by formula:

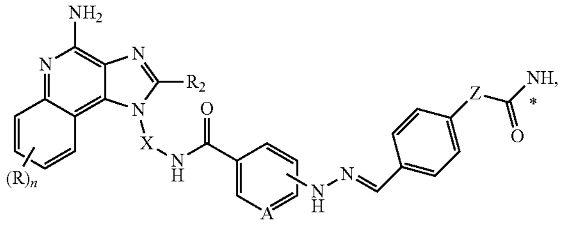

wherein:

X is alkylene having up to 8 carbon atoms optionally interrupted or terminated by —O—;

$R_2$ is hydrogen, alkyl, alkoxyalkylenyl, alkylaminoalkylenyl, or hydroxyalkylenyl;

A is CH or N:

R is halogen, hydroxyl, alkyl, haloalkyl, or alkoxy;

n is an integer from 0 to 4;

Z is a bond or —C(O)—NH—$(CH_2CH_2O)_p$—$CH_2CH_2$—, wherein p is in a range from 1 to 50; and the nitrogen atom indicated by N* is covalently bonded to the antigen;

or a pharmaceutically acceptable salt thereof.

13. A pharmaceutical composition comprising a pharmaceutically acceptable carrier and a conjugate of claim 8.

14. A method of vaccinating an animal, the method comprising administering an effective amount of the conjugate of claim 8 to the animal.

15. A method of inducing cytokine biosynthesis in an animal, the method comprising administering an effective amount of the conjugate of claim 8 to the animal.

16. A composition comprising the compound or salt of claim 1, an aldehyde-bearing antigen, and a pharmaceutically acceptable carrier.

17. A method of making a conjugate, the method comprising:

combining a compound or salt of claim 1, wherein P is a protected amino group; an aldehyde-bearing antigen; and a carrier under conditions where the protected amino group is deprotected and the conjugate is formed.

18. The conjugate of claim 12, wherein Z is a bond.

19. The conjugate of claim 12, wherein Z is —C(O)—NH—$(CH_2CH_2O)_p$—$CH_2CH_2$—, wherein p is in a range from 1 to 50.

20. A pharmaceutical composition comprising a pharmaceutically acceptable carrier and a conjugate of claim 12.

* * * * *